United States Patent [19]
Burck et al.

[11] Patent Number: 5,242,688
[45] Date of Patent: Sep. 7, 1993

[54] METHOD OF TREATING THROMBOEMBOLIC DISORDERS BY ADMINISTRATION OF DIGLYCOSYLATED T-PA VARIANTS

[75] Inventors: Philip J. Burck; Charles V. Jackson; Gerald F. Smith, all of Indianapolis, Ind.

[73] Assignee: Eli Lilly and Company, Indianapolis, Ind.

[21] Appl. No.: 633,584
[22] Filed: Dec. 24, 1990
[51] Int. Cl.$^5$ .................... A61K 37/547; C12N 9/68; C12N 9/70
[52] U.S. Cl. ................ 424/94.64; 435/212; 435/216
[58] Field of Search .............. 424/94.64; 435/212, 435/216

[56] References Cited

U.S. PATENT DOCUMENTS

| | | |
|---|---|---|
| 4,751,084 | 6/1988 | Feder et al. ......... 424/94.64 |
| 4,927,630 | 5/1990 | Feder et al. ......... 424/94.64 |
| 4,935,237 | 6/1990 | Higgins et al. ....... 424/94.64 |
| 4,970,159 | 11/1990 | Dodd ................ 435/226 |
| 5,002,887 | 3/1991 | Larsen .............. 424/94.64 |
| 5,037,646 | 8/1991 | Higgins et al. ....... 424/94.64 |
| 5,089,409 | 2/1992 | Howard et al. ........ 435/212 |

FOREIGN PATENT DOCUMENTS

| | | |
|---|---|---|
| 0225286 | 6/1987 | European Pat. Off. |
| 0238304 | 9/1987 | European Pat. Off. |
| 0297066 | 12/1988 | European Pat. Off. |
| 0311589 | 4/1989 | European Pat. Off. |
| 63-230083A | 9/1988 | Japan . |
| WO84/01786 | 5/1984 | World Int. Prop. O. |
| 88/10119 | 12/1988 | World Int. Prop. O. |
| WO89/04368 | 5/1989 | World Int. Prop. O. |
| WO89/09266 | 10/1989 | World Int. Prop. O. |
| WO89/11531 | 11/1989 | World Int. Prop. O. |

OTHER PUBLICATIONS

Burck, et al., 1990, *J. Biological Chemistry* 265:5170–5177.
Jackson, et al., 1990, *Circulation* 82(3):930–940.
Wittmer and Howard, 1990 *Biochemistry* 29:4175–4180.
Parekh, et al., 1989, *Biochemistry* 28:7644:7662.
Parekh, et al., 1989, *Biochemistry* 28:7670–7679.
Wittwer, et al., 1989, *Biochemistry* 28:7662–7669.
Wu, et al., 1990, *J. Cardiovascular Pharmacology* 16:197–203.
Spellman, et al., 1989, *J. Biological Chemistry* 264(24):14100–14111.
Higgins and Bennett, 1990, *Annu. Rev. Pharmacol. Toxicol.* 30:91–121.
Pohl, et al., 1987, *Eur. J. Biochem.* 170:69–75.
Larsen, et al., 1989, *Blood* 73(7):1842–50.
Collen, et al., 1988, *Blood* 71(1):216–219.
Cambier, et al., 1988, *J. of Cardiovascular Pharmacology* 11:468–472.
Larsen, et al., 1988, *J. of Biological Chemistry* 263(2):1023–1029.
Hansen, et al., 1988, *J. of Biological Chemistry* 263(30):15713–15719.
Lau, et al., 1987, *Bio/Technology* 5:953–958.
Hotchkiss, et al., 1988, *Thrombosis and Haemostasis* 60(2):255–261.
Haigwood, et al., 1989, *Protein Engineering* 2(8):611–620.
Wilhelm, et al., 1990, *Thrombosis and Haemostasis* 63(3):464–471.
Johannessen et al., *Thrombosis & Hemostasis* 63:54–59, Feb. 19, 1990.
Urano et al., *Proc. Natl. Acad. Sci.* 86:2568–2571, Apr. 1989.
Van Zonneveld et al., *J. Cell. Biochem* 32:169–178, 1986.
Van Zonneveld et al., *Proc. Natl. Acad. Sci.* 83:4670–4674, Jul. 1986.
Van Zonneveld et al., *J. Biol. Chem.* 261:14214–14218, Oct. 25, 1986.
Gething et al., *Embo Journal* 7:2731–2740, 1988.
Browne et al., *Fibrinolysis* 3:207–214, 1989, as Abstracted in *Biological Abstracts* 89:AB-100, Ref. No. 21772, 1 Feb. 1990.

*Primary Examiner*—Robert A. Wax
*Assistant Examiner*—Stephen Walsh
*Attorney, Agent, or Firm*—Thomas G. Plant; Leroy Whitaker

[57] ABSTRACT

The present invention provides a method of treating thromboembolic disorders with the diglycosylated form of a tissue plasminogen activator derivative that lacks the Finger, EGF and Kringle I domains of the native tissue plasminogen activator molecule.

11 Claims, 17 Drawing Sheets

METHOD OF TREATING THROMBOEMBOLIC DISORDERS BY ADMINISTRATION OF DIGLYCOSYLATED T-PA VARIANTS

FIELD OF THE INVENTION

This invention relates to a method of using a diglycosylated form of a tissue plasminogen activator derivative that lacks the Finger, Growth Factor and Kringle 1 domains in the treatment of thromboembolic disorders.

BACKGROUND OF THE INVENTION

Plasminogen activators are a unique class of enzymes that convert plasminogen to its active enzymatic form, plasmin. Plasmin is a serine protease that degrades the fibrin networks of blood clots. Several plasminogen activators are currently being used as in vivo fibrinolytic agents in the treatment of acute myocardial infarction. One of these plasminogen activators, tissue plasminogen activator (t-PA), has a significantly enhanced ability to activate plasminogen in the presence of fibrin. Thus, when used as an in vivo fibrolytic agent, t-PA is directed to fibrin clots.

Human t-PA is a multi-domain serine protease secreted by vascular endothelial cells. Five distinct structural domains make up the 527 amino acids of the mature t-PA molecule. The molecule is synthesized as a one-chain polypeptide that can be converted to the two-chain form by a plasmin-mediated cleavage at Arginine 275-Isoleucine 276. The DNA and amino acid structure of human t-PA was described by Pennica et al., 1983, *Nature* 301:214. The numbering system employed by Pennica et al. is used herein. Gene mapping studies of genomic t-PA have shown that the gene encoding t-PA is comprised of twelve exons split by introns (Ny et al., 1984, *Proc. Natl. Acad. Sci. USA* 81:5355). These introns correspond, in part, with the domain junctions at the amino acid level.

The amino-terminal portion of the molecule contains a disulfide-linked loop referred to as the Finger domain (F). This domain is highly homologous to the Finger domain of fibronectin that provides this molecule with fibrin-binding properties. The second domain, called the Growth Factor domain (E), is highly homologous with epidermal growth factor. Similar growth factor domains occur in serine proteases such as urokinase, protein C and clotting factors IX and X. The third and fourth domains are highly disulfide-linked structures referred to as Kringles (K1 and K2). Similar Kringle structures are present in plasma proteins such as plasminogen and prothrombin. There is conflicting evidence as to whether both Kringle domains or just the second Kringle domain are involved in the fibrin-mediated activation of plasminogen. The fifth domain, located at the carboxy-terminus, is the Serine Protease domain (SP). The Serine Protease domain is homologous to similar domains in urokinase, plasma serine clotting proteases and trypsin.

There has been significant growth in the acceptance of thrombolytic therapy for the early restoration of blood flow to ischemic myocardium. Because of a short plasma half-life, recombinant tissue plasminogen activator must be administered by intravenous infusion to insure thrombolytic efficacy. Recent reviews of coronary thrombolysis suggest that the ideal properties for a new thrombolytic agent are that it be fibrin specific, have a longer plasma half-life allowing for a single injection administration, produce more rapid reperfusion, prevent reocclusion and be safer (i.e. lower bleeding risk, non-immunogenic), than streptokinase, t-PA or urokinase (Collen, D., *Klin. Wochenschr.* 1988; 66 (Suppl. 12):15-23; Bang et al., 1989, *Annu. Rev. Pharmacol. Toxicol.* 29:322-341; Minno et al., 1989, *Pharmacol. Res.* 21(2):153-161; Mueller et al., 1989, *Med. Clin. North Am.* 73(2):387-407).

Since the production of recombinant t-PA, investigators have produced modified recombinant forms of t-PA and urokinase in an attempt to learn more about these serine proteases (Krause, J., 1988, *Fibrinolysis* 2:133-142; Pannekoek et al., 1988, *Fibrinolysis* 2:123-133; Haigwood et al., 1989, *Protein Engineering* 2:611-620; Higgins and Bennett, 1990, *Annu. Rev. Pharmacol. Toxicol.* 30:91). A major emphasis in the design of derivative forms has been to increase fibrin specificity, increase circulating plasma half-life, and decrease bleeding liability compared with endogenous natural enzymes.

One derivative of native t-PA was described by Burck et al., 1990, *Journal of Biological Chemistry* 265(9):5176. This derivative, known as mt-PA6, was constructed by site-specific mutagenesis of the cDNA encoding human t-PA. The DNA encoding amino acids 4-175 was deleted so that upon expression the resultant t-PA derivative comprised the signal peptide and propeptide domains, the first three amino acids of mature t-PA, as well as the Kringle 2 and Serine Protease domains. mt-PA6 was found to possess greater fibrinolytic activity and a greater ability to activate thrombus bound plasminogen than native t-PA (Jackson et al., 1990, *Circulation* 82: 930-940).

t-PA derived from melanoma cells and produced by recombinant DNA methods from CHO cells, comprises four consensus Asparagine-linked (N-linked) glycosylation sites at amino acids 117, 184, 218 and 448. In native t-PA amino acid 184 is glycosylated only part of the time while amino acid 218 is not glycosylated (Higgins and Bennett, 1990). Thus, two glycosylation forms of native t-PA have been isolated. One form is glycosylated at amino acid 117 in the Kringle 1 domain and amino acid 448 in the Serine Protease domain. The second form is glycosylated at amino acids 117, 448 and 184.

The oligosaccharides at amino acids 184 and 448 are complex oligosaccharides while amino acid 117 is occupied by a high-mannose oligosaccharide (Spellman et al., 1989, *J. of Biol. Chem.* 264(24):14100). The structures of these oligosaccharides in native t-PA derived from CHO cells was described by Spellman et al., 1989. N-linked glycosylation sites are tripeptide sequences that are specifically recognized and glycosylated. Examples of tripeptide consensus sequences include asparagine-X-threonine and asparagine-X-serine, wherein X is any amino acid but proline.

When produced by eukaryotic cell culture, mt-PA6 is also found in two glycosylated forms. These two forms account for the doublet of 40 and 42 kD bands seen when the purified enzyme is analyzed by gel electrophoresis. Primary mt-PA6 is glycosylated only at amino acid 448. Variant mt-PA6 is glycosylated at amino acids 448 and 184. mt-PA6 lacks the K1 domain and, therefore, the glycosylation site at amino acid 117. No glycosylation is found at amino acid 218 in Kringle 2. Variant mt-PA6 comprises 15-25% of the mt-PA6 molecules secreted from a Syrian hamster cell line (Burck et al., supra).

Studies on the effect of altering glycosylation patterns of t-PA derivatives (wherein the Finger and Growth Factor domains had been deleted) indicate that derivatives which are partially or totally non-glycosylated have a higher fibrinolytic versus fibrinogenolytic ratio than their fully glycosylated counterparts (Hansen et al., 1988, *Journal of Biological Chemistry* 263(30): 15713-19). These results teach away from the method of the present invention. Diglycosylated t-PA derivatives lacking the Finger, EGF and Kringle 1 domains, especially Variant mt-PA6, provide advantages over their partially and nonglycosylated counterparts in the treatment of thromboembolic disorders. Variant mt-PA6 displays the unexpected and advantageous properties of causing less systemic conversion of plasminogen to plasmin, is markedly less prone to metabolism to its two-chain form, and has a higher fibrinolytic versus fibrinogenolytic ratio than Primary mt-PA6. Surprisingly, Variant mt-PA6 also provides a greater maintenance of coronary blood flow.

For purposes of the present invention, as disclosed and claimed herein, the following terms are defined below.

ApR—the ampicillin-resistant phenotype or gene conferring same.

ElA—an immediate-early gene product of adenovirus which can activate a poly-GT element to express enhancer activity and can also activate the BK virus enhancer.

ep—a DNA segment comprising the SV40 early promoter of the T-antigen gene, the T-antigen binding sites, and the SV40 origin of replication.

GBMT transcription control unit—a modified transcription control unit that comprises the P2 enhancer element of BK virus spaced closely to the upstream regulatory element of the major late promoter of adenovirus (MLTF), the adenovirus-2 major late promoter and a poly-GT element positioned to stimulate said promoter and a DNA sequence encoding the spliced tripartite leader of adenovirus-2. The GMBT transcription control unit is best exemplified by the approximately 900 base pair HindIII cassette found in plasmid pGTC which is found in *E. coli* K-12 AG1/pGTC (NRRL B-18593).

GT—enhancer system—any poly-GT element linked to a promoter, such as MLP, in which the poly-GT element does not itself possess enhancer activity but is activated as an enhancer by an immediate-early gene product of a large DNA virus, such as the ElA gene product or by any similarly activating viral gene product.

HmR—the hygromycin-resistant phenotype or gene conferring same.

IVS—DNA encoding an intron, also called an intervening sequence.

Large DNA virus—a virus that infects eukaryotic cells and has a genome greater than ~10 kb in size, i.e., any of the pox viruses, adenoviruses, and herpes viruses.

MLP—the major late promoter of adenovirus, that is also referred to herein as the adenovirus late promoter, adenovirus-type-2 late promoter, or Ad2 late promoter.

MLTF binding site—the site in adenovirus DNA where the major late transcription factor (MLTF) binds; the MLTF is required for MLP activity.

N-linked glycosylation—the attachment of oligosaccharides to a protein through an N-glycosidic bond with the asparagine residue in an Asn-X-Ser/Thr sequence.

NeoR—the neomycin resistance-conferring gene, which can also be used to confer G418 resistance in eukaryotic host cells.

ori—a plasmid origin of replication.

pA—a DNA sequence encoding a polyadenylation signal.

Poly-GT element—a DNA sequence of $(GT)_n$-$(CA)_n$, which is illustrated herein by a sequence where n is 21, but which can also refer to sequences of varying lengths where n is greater or less than 21, and may refer to chemically synthesized $(GT)_n$-$(CA)_n$ sequences or human genomic DNA fragments containing a $(GT)_n$-$(CA)_n$ tract.

Reocclusion—complete cessation of blood flow after successful thrombolysis caused by reformation of thrombus and/or vasoconstriction.

Reperfusion—restoration of blood flow caused by successful thrombolysis.

SUMMARY

Figure 1:
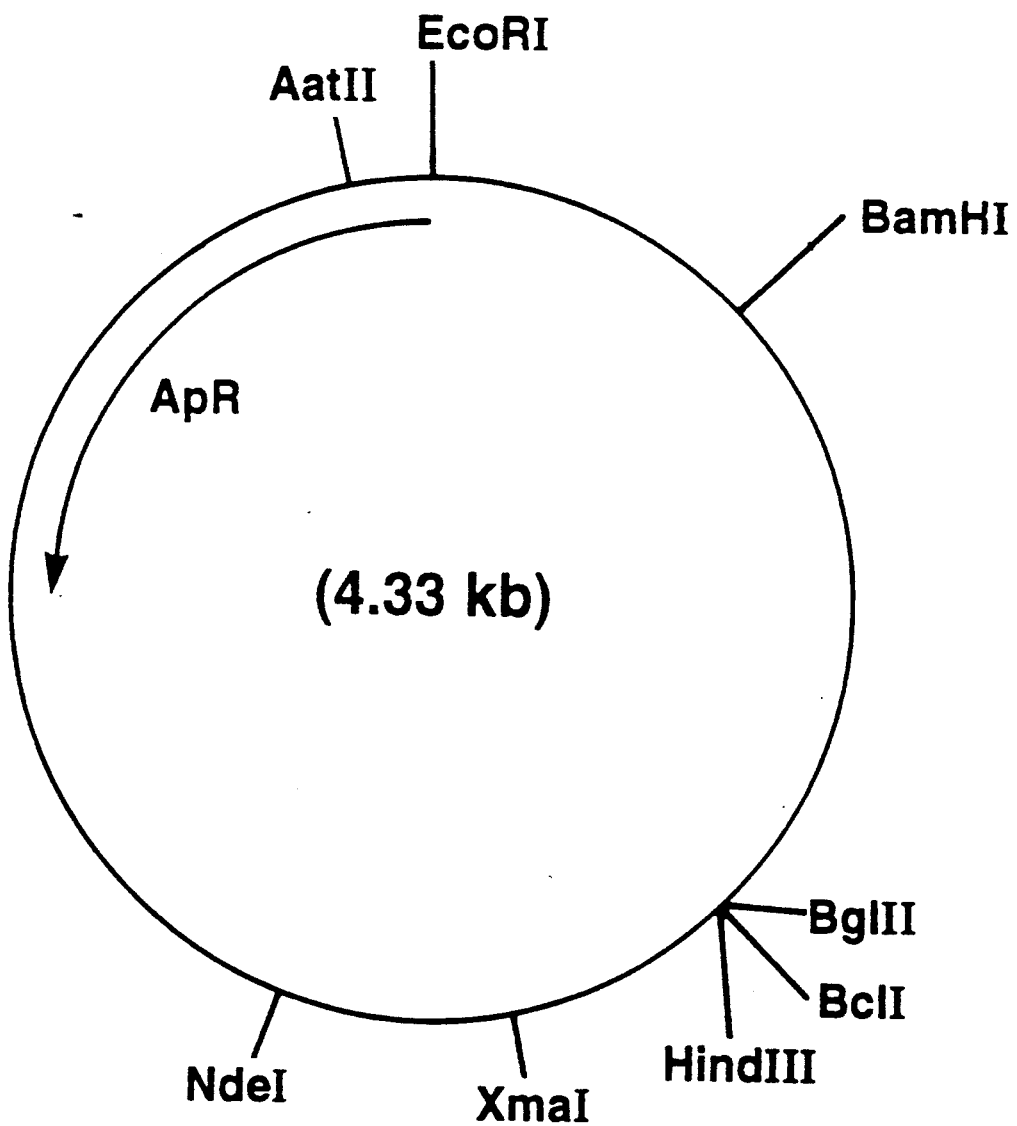
FIG. 1 is a restriction and function map of pLP53.

The present invention provides a method of treating thromboembolic disorders by administration of an effective dose of a diglycosylated t-PA derivative wherein said derivative lacks the Finger, Growth Factor and Kringle 1 domains. Preferably, the method of treatment of thromboembolic disorders is by the administration of an effective dose of Variant mt-PA6.

The method further provides for the use of a diglycosylated t-PA derivative, wherein said t-PA derivative lacks the Finger, EGF and Kringle 1 domains, as a pharmaceutical in the treatment of thromboembolic disorders including deep vein thrombosis, disseminated intravascular coagulation, emboli originating from the heart or peripheral arteries, acute myocardial infarction, thrombotic strokes, and fibrin deposits associated with invasive cancers.

The present invention provides an improvement over current therapies by providing a plasminogen activator that possesses the highly desirable properties of sparing plasminogen and fibrinogen while displaying a longer in vivo half-life and providing greater maintenance of coronary blood flow.

DETAILED DESCRIPTION

When produced by recombinant DNA technology from eukaryotic cell culture, t-PA derivatives that lack the Finger, EGF and Kringle 1 domains, such as mt-PA6, are found in both monoglycosylated (Primary) and diglycosylated (Variant) forms. The present invention provides the art with the method of treating thromboembolic disorders with the diglycosylated form of a t-PA derivative that lacks the Finger, EGF and Kringle 1 domains.

Variant mt-PA6 is the preferred embodiment of the present invention and is illustrative of diglycosylated t-PA derivatives lacking the Finger, EGF and Kringle 1 domains of native t-PA. The gene encoding mt-PA6 was constructed and cloned into an expression vector resulting in the plasmid pmt6-hd as described in Example 2. Plasmid pmt6-hd was transformed into Syrian hamster AV12-664 cells by conventional eukaryotic cell transformation techniques. The transformed cells were cultured and mt-PA6 was isolated and purified from the culture medium as described by Burck et al., supra.

For the purpose of exemplifying the usefulness of the present invention, a sample of mt-PA6 that contained greater than 85% Variant mt-PA6 was compared to a sample of mt-PA6 that contained greater than 92% Primary mt-PA6. The two forms of mt-PA6 can be separated by affinity chromatography in substantial accordance with the method by Einarsson et al., 1985, *Biochim. Biophys. Acta* 830:1-10, and Rijken et al., 1985, *Thromb. and Haemostas.* 54(4), 788-791. The thrombolytic potential of Variant mt-PA6 was studied in a canine thrombosis model as described by Jackson et al. (Jackson et al., 1990, *Circulation* 82: 930-940). The role of Variant mt-PA6 in fibrinogen degradation and plasminogen degradation was also examined by the methods described by Jackson et al., supra.

Marked pharmacological distinctions were found between Variant and Primary mt-PA6. Treatment with Primary mt-PA6 resulted in systemic activation of plasminogen and loss of plasma fibrinogen. In striking contrast, Variant mt-PA6 produced no systemic plasminogen activation, no fibrinogen degradation and was less susceptible to metabolism to the two-chain form. Surprisingly, Variant mt-PA6 also provided greater maintenance of coronary blood flow.

mt-PA6-encoding DNA was inserted into a multi-cistronic vector in which the expression of mt-PA6 was driven by the E1A responsive BL transcriptional unit. The resulting plasmid also contained cistrons for the expression of the DNA encoding hygromycin phosphotransferase and dihydrofolate reductase (DHFR), both driven by the SV40 early promoter.

Amino acids -13 to -35 of t-PA are hydrophobic amino acids comprising a signal sequence that directs secretion of the t-PA molecule from the host cell (Vehar et al., 1984, *Bio/Technology* 2(12):1050). This signal sequence is cleaved from the t-PA molecule during the secretion process, yielding a t-PA molecule with a 12 amino acid propeptide extension at the amino-terminal end. When t-PA is produced by melanoma cells using cell culture techniques, the t-PA molecules isolated from the resulting culture medium exist in two forms (Wallen et al., 1983, *Eur. J. Biochem.* 132:681-686). One form is a t-PA molecule from which 9 of the 12 amino acids of the propeptide have been cleaved, resulting in a t-PA molecule with the tripeptide amino-terminal extension H$_2$N-Gly-Ala-Arg. A second form is a fully processed mature t-PA from which the entire propeptide region has been cleaved (Vehar et al., 1984). mt-PA6 is also found in culture medium in the partially and fully processed forms. No differences were observed in the in vitro activity of the two amino-terminus forms of mt-PA6 (Burck et al., supra).

The heterogeneity at the amino-terminus can be eliminated by providing a propeptide region that is capable of being uniformly cleaved by a cell associated protease. U.S. patent application Ser. No. 07/609,510, filed Nov. 6, 1990, describes compounds and methods that allow the production of a homogeneous population of t-PA molecules. The amino acid sequence of the propeptide cleavage can be encoded by the following amino acid sequences that are positioned to directly precede amino acid +1 (Ser) of the mature t-PA molecule: Arg Ile P3 P2 P1 (SEQ ID NO: 1); Ser Arg P3 P2 P1 (SEQ ID NO: 2); Glu Arg P3 P2 P1 (SEQ ID NO: 3); and Val Arg P3 P2 P1 (SEQ ID NO: 4) wherein the amino acids at positions P3, P2 and P1 are Lys or Arg. The more preferred uniformly cleavable cell associated protease cleavage sites are: Arg Ile Arg Lys Arg (SEQ ID NO: 5); Ser Arg Lys Arg Arg (SEQ ID NO: 6); Glu Arg Arg Lys Arg (SEQ ID NO: 7); Val Arg Lys Arg Arg (SEQ ID NO: 8). The most preferred uniformly cleavable cell associated protease cleavage sequence is SEQ ID NO: 5. The DNA sequence encoding these cleavage sequences can be incorporated into the recombinant DNA vectors encoding the t-PA molecules. The skilled artisan will recognize that incorporation of these DNA sequences can be carried out by methods well known in the art, such as site-specific mutagenesis (described by Maniatis et al. 1989). Thus, the Variant form of mt-PA6 can be produced such that the amino-terminus of the molecules lacks the tripeptide sequence H$_2$N-Gly-Ala-Arg.

The plasmid pSBL-Bt6 was constructed to provide high level expression of mt-PA-6 linked to the novel propeptide regions. Expression is provided by this plasmid from the SBL unit which comprises the SV40 enhancer linked to the P2 enhancer of BK virus that is spaced closely to the adenovirus-2 late promoter. The SBL unit will drive high levels of expression of a useful substance that is properly positioned. The plasmid pSBL-Bt6 has the SBL unit properly positioned to express mt-PA-6 that is operably linked to the uniformly cleavable propeptide regions.

To further exemplify the present invention, the plasmid pGT-t6B-d was constructed. This plasmid enables high level expression of mt-PA-6 linked to the uniformly cleavable propeptide regions. Expression is provided by this plasmid from the GBMT unit that comprises the P2 enhancer of BK virus spaced closely to the upstream regulatory element of the major late promoter of adenovirus (MLTF), the adenovirus-2 late promoter, a poly-GT element positioned to stimulate said promoter and a DNA sequence encoding the tripartite leader sequence of adenovirus. When properly positioned, the GBMT unit will drive high levels of expression of a useful substance. The plasmid pGT-t6B-d has the GBMT unit properly positioned to express mt-PA-6.

It is preferable to transform the above vectors into host cells that express the adenovirus E1A immediate-early gene product, in that the BK enhancer found on the vectors functions to enhance expression most efficiently in the presence of E1A. Skilled artisans will recognize that a number of host cells express, or can be made to express, an immediate-early gene product of a large DNA virus such as E1A. Preferred cell lines are the Syrian Hamster line AV12-664 (available from the American Type Culture Collection (ATCC), Rockville Md., 20852 under the accession number CRL 9595) or the human kidney 293 cell line (ATCC CRL 1573). The AV12-664 cell line is most preferred.

The vectors useful in the present invention can be transformed into and expressed in a variety of eukaryotic host cells. Vectors of the invention that possess no selectable marker with which to identify and isolate stable eukaryotic transformants are useful not only for purposes of transient assay but also for purposes of cotransformation, a procedure disclosed in U.S. Pat. No. 4,399,216, issued Aug. 26, 1983, and incorporated herein by reference. In addition, the vectors may further comprise sequences that allow for replication in *Escherichia coli*, as it is usually more efficient to prepare plasmid DNA in *E. coli* than in other host organisms.

Expression of the t-PA derivatives encoded by the vectors of the present invention occurs in those host cells in which the particular promoter associated with the t-PA derivative gene functions. Exemplary host cells suitable for use in the invention include BHK-21 cells (ATCC CRL 10), CHO-K1 cells (ATCC CRL 61) and C127I cells (ATCC CRL 1616).

Many mammalian host cells possess the necessary cellular machinery for the recognition and proper processing of the signal peptide on the nascent proteins of the invention and provide the post-translational modifications, such as glycosylation. A wide variety of vectors, discussed below, exist for the transformation of such eukaryotic host cells, and the specific vectors exemplified below are in no way intended to limit the scope of the present invention.

The pSV2-type vectors comprise segments of the SV40 genome that constitute a defined eukaryotic transcription unit-promoter (ep), intervening sequence (IVS), and polyadenylation (pA) site. In the absence of SV40 T-antigen, the plasmid pSV2-type vectors transform mammalian and other eukaryotic host cells by integrating into the host cell chromosomal DNA. A variety of plasmid pSV2-type vectors have been constructed (see *Eukaryotic Viral Vectors*, edited by Gluzman, published by Cold Spring Harbor Laboratories, Cold Spring Harbor, N.Y., 1982), such as plasmids pSV2-gpt, pSV2-neo, pSV2-dhfr, pSV2-hyg, and pSV2-β-globin, in which the SV40 promoter drives transcription of an inserted gene. These vectors are suitable for use with the coding sequences of the invention and are available either from the American Type Culture Collection (ATCC) in Rockville, Md. or from the Northern Regional Research Laboratory (NRRL) in Peoria, Ill.

Plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification, described in a review article by Schimke, 1984, *Cell* 37:705–713, can involve DNA sequences closely contiguous with the dhfr gene, such as the t-PA compounds of the present invention, and thus can be used to increase production of the t-PA molecules of the invention.

Plasmids that were constructed for expression of the t-PA compounds of the invention in mammalian and other eukaryotic host cells can utilize a wide variety of promoters. The present invention is in no way limited to the use of the particular eukaryotic promoters exemplified herein. Promoters such as the SV40 late promoter or the eukaryotic promoters disclosed in Bucher et al., 1986, *Nuc. Acids Res.* 14(24):1009, or promoters from eukaryotic genes, such as, for example, the estrogen-inducible chicken ovalbumin gene, the interferon genes, the glucocorticoid-inducible tyrosine aminotransferase gene, the thymidine kinase gene, and the major early and late adenovirus genes, can be readily isolated and modified for use on recombinant DNA expression vectors designed to produce human tissue plasminogen activator in eukaryotic host cells. Eukaryotic promoters can also be used in tandem to drive expression of a coding sequence of the invention. Furthermore, a large number of retroviruses are known that infect a wide range of eukaryotic host cells. The long terminal repeats in the retrovirus DNA often encode promoter activity and thus can be used to drive expression of the coding sequences of the invention.

Plasmid pRSVcat (ATCC 37152) comprises portions of the long terminal repeat of the Rous Sarcoma virus (RSV), a virus known to infect chicken and other host cells. The RSV long terminal repeat sequences can be isolated on an ~0.76 kb NdeI-HindIII restriction fragment of plasmid pRSVcat. The promoter in the RSV long terminal repeat (Gorman et al., 1982, *Proc. Natl. Acad. Sci. USA* 79:6777) is suitable for use in vectors of the invention. Plasmid pMSVi (NRRL B-15929) comprises the long terminal repeats of the Murine Sarcoma virus (MSV), a virus known to infect mouse and other host cells. These repeat sequences are suitable for use as a promoter in the vectors of the invention. The mouse metallothionein (MMT) promoter has also been well characterized for use in eukaryotic host cells and is suitable for use in the vectors of the invention. The MMT promoter is present in the 15 kb plasmid pdBPV-MMTneo (ATCC 37224) which can serve as the starting material for the construction of other plasmids of the present invention.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human t-PA and can be constructed by conventional synthetic or site-specific mutagenesis procedures. Synthetic DNA methods can be carried out in substantial accordance with the procedures of Itakura et al., 1977, *Science* 198:1056 and Crea et al., 1978, *Proc. Natl Acad. Sci. USA* 75:5765. Site-specific mutagenesis procedures are described in Maniatis et al., *Molecular Cloning: A Laboratory Manual* Cold Spring Harbor, N.Y. (2d ed. 1989). Therefore, the present invention is in no way limited to the DNA sequences and plasmids specifically exemplified.

After transformation of a vector of the present invention into a eukaryotic host cell, one can select transformants on the basis of a selectable phenotype. This phenotype can be conferred either by a selectable marker present on the expression vector or present on another vector cotransformed with the expression vector into the host cell. Once transformants are selected, it is desirable to identify which transformants are expressing the highest levels of the desired protein encoded on the expression vector. Such identification is especially important after a cotransformation procedure, which generates a number of transformants that contain only the plasmid containing the selectable marker and so do not contain the expression vector.

The use of the dihydrofolate reductase (dhfr) gene as a selectable marker for introducing a gene or plasmid into a dhfr-deficient cell line and the subsequent use of methotrexate to amplify the copy number of the plasmid has been well established in the literature. Although the use of the dhfr-producing cells has not been well studied, efficient coamplification in primate cells requires initial selection using a directly selectable marker before the coamplification using methotrexate. The use of the present invention is not limited by the selectable marker used. Moreover, amplifiable markers such as the metallothionein genes, adenosine deaminase genes, or members of the multigene resistance family, exemplified by P-glycoprotein, can be utilized.

The diglycosylated t-PA derivatives of the present invention are attractive alternatives to conventional thrombolytic agents in the treatment of thromboembolism in the immediate postsurgical period because of the lower likelihood of bleeding complications. The diglycosylated t-PA derivatives may be used prior to or in conjunction with thrombectomies and embolectomies, surgical procedures which are often necessary to save ischemic limbs from amputation in the setting of an acute arterial obstruction.

Arterial emboli originating from the heart are frequent complications in diseases of the heart involving heart valves, in patients with artificial heart valves, in acute myocardial infarction and in certain types of heart arrhythmias. The treatment of these problems with conventional thrombolytic agents is frequently ineffective; the risk of bleeding complications is substantial particularly if the embolus is lodged in a major cerebral artery. The diglycosylated t-PA derivatives of the present invention are highly effective thrombolytic agents that carry a low risk of bleeding complications and have substantial utility in the treatment of cardiogenic emboli.

Similarly, emboli originating from thrombi in peripheral arteries, most notably the carotid arteries, can be treated with conventional thrombolytic agents only at extremely high risk to the patient for major intracerebral bleeding complications. The diglycosylated t-PA derivatives of the present invention with their reduced potential for bleeding complications may well have utility in this clinical situation.

The diglycosylated t-PA derivatives of the present invention may also be useful in the treatment of thrombotic strokes, particularly the so-called "stroke in evolution." Conventional thrombolytic agents given to patients with completed strokes or "strokes in evolution" had disastrous consequences in the form of severely debilitating or fatal intracerebral bleeds. Similarly, treatment of strokes with either heparin or oral anti-coagulants, although occasionally beneficial, carry a high risk for bleeding into the infarcted brain area thereby aggravating the neurological deficit accompanying the stroke. Because of their low potential for causing bleeding complications and their selectivity, it is expected that the diglycosylated t-PA derivatives of the present invention can be given to stroke victims and will be beneficial in dissolving the occluding thrombus, thereby reducing the neurological deficit resulting from the stroke, provided the agent is administered early enough after the onset of symptoms.

The diglycosylated t-PA derivatives of the present invention will be useful treatments in acute myocardial infarction. As has been demonstrated, authentic t-PA when administered I.V. in doses of 30–100 mg over 1–3 hours is effective in dissolving occluding coronary thrombi, reestablishing myocardial perfusion and salvaging large areas of ischemic myocardium.

Evidence has been presented in experimental animals that the conventional thrombolytic agents streptokinase, plasmin and urokinase are useful in the treatment of invasive malignant tumors. Many tumor cells produce substances that trigger the activation of the coagulation system resulting in localized fibrin deposits. These fibrin deposits function as "nests" in which cancer cells can divide to form mestastatic lesions. The lysis of these fibrin deposits are thought to prevent the growth of metastatic malignancies. Conventional thrombolytic agents given to patients with widespread cancers probably pose an unacceptable risk for bleeding complications. Patients with invasive cancers are usually placed on aggressive chemotherapeutic regimens resulting in profound thrombocytopenia, and the combined effects of thrombocytopenia and a fibrinolytic coagulation defect unquestionably will produce severe bleeding problems in the majority of patients. Because of a low potential for bleeding complications and high selectivity, it is likely that the diglycosylated t-PA derivatives of the present invention can be given safely to patients who are thrombocytopenic as the result of aggressive cancer chemotherapy.

It has been postulated that sizable numbers of patients develop venous thromboembolism because of defective synthesis and/or secretion of endothelial cell derived t-PA. In the past, such patients have been treated effectively with a combination of anabolic steroids and phenformin which results in an increase in intrinsic t-PA synthesis. This long-term regimen was found to sharply reduce the incidence of recurrent deep-vein thrombosis, pulmonary embolism or both; however, this therapeutic regimen was abandoned because of an unacceptably high risk of serious side effects. The diglycosylated t-PA derivatives of the present invention administered by bolus intravenous injection or through continuous infusion using light weight portable pump systems may have substantial utility in the prevention of recurrent thromboembolic events in suitably selected patients.

The diglycosylated t-PA derivatives of the present invention can be formulated according to known methods to prepare pharmaceutically useful compositions, whereby the diglycosylated t-PA derivative is combined in admixture with a pharmaceutically acceptable carrier vehicle. Suitable carrier vehicles and their formulation, inclusive of other human proteins, e.g., human serum albumin, are described for example, in *Remington's Pharmaceutical Sciences* 16th ed., 1980, Mack Publishing Co., edited by Oslo et al., which is incorporated by reference. Such compositions will contain an effective amount of a diglycosylated t-PA derivative of the present invention together with a suitable amount of carrier vehicle to prepare pharmaceutically compositions suitable for effective administration to the host. Such compositions can be administered parentally, or by other means that ensure its delivery to the bloodstream in an effective form. The preferred method of administration of the diglycosylated t-PA derivatives of the present invention is by bolus intravenous administration. Preferred dosages range from about 0.01 mg/kg to 10 mg/kg. More preferred dosages range from about 0.1 mg/kg to 1 mg/kg. The most preferred dosage is about 0.4 mg/kg.

BGT3 (SEQ ID NO: 9)
5'-GATCCGCCACCATGGATGCAATGAAGAGAGGGCTCTGCTGTGTGCTGCTGCTG
TGTGGAGCAGTCTTCGTTTCGCCCAGCCAGGAAATCCATGCCCGATTCAGAATCCG
CAAAA-3'

BGT4 (SEQ ID NO:10)
5'-GATCTTTTGCGGATTCTGAATCGGGCATGGATTTCCTGGCTGGGCGAAACGAAG
ACTGCTCCACACAGCAGCAGCACACAGCAGAGCCCTCTCTTCATTGCATCCATGGTG
GCG-3'.

The following examples are intended to assist in further understanding of the invention. Particular materials employed, species and conditions are intended to be further illustrative of the invention and not limiting the reasonable scope thereof. Enzymes referred to in the examples are available, unless otherwise indicated from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250 and are used in substantial accordance with the manufacturer's recommendations. Many of the techniques employed herein are well known to the artisan of ordinary skill. Molecular biology techniques are described in detail in laboratory manuals such as Maniatis et al., *Molecular Cloning: A Laboratory Manual* Cold Spring Harbor, N.Y. (2d ed. 1989) and *Current Protocols in Molecular Biology* (Ausubel et al. eds. 1987). The skilled artisan will recognize that alternate procedures can be substituted for various procedures presented below.

Example 1

Construction of pLP53-TLB

A. Preparation of BamHI-BglII Digested pLP53

The plasmid pLP53 can be conventionally isolated from *Escherichia coli* K12 AG1/pLP53 according to the method of Example 1F. *E. coli* K12 AG1/pLP53 was deposited on Sep. 21, 1990 and made part of the permanent stock culture collection of the Northern Regional Research Center (NRRL), Agriculture Research Service, U.S. Department of Agriculture, Peoria, Ill. 61604 under accession number NRRL B-18714. A restriction site and function map of pLP53 is shown in FIG. 1.

Five $\mu l$ (5 $\mu g$) of pLP53 DNA was digested to completion with 2 $\mu l$ (20 units) of BamHI and 2 $\mu l$ (20 units) of BglII in a 50 $\mu l$ reaction volume containing 50 mM Tris-HCl (pH 8.0) (Tris is tris[hydroxymethyl]aminomethane), 10 mM $MgCl_2$ and 50 mM NaCl. The reaction was incubated at 37° C. for two hours. The sample was extracted twice with an equal volume of a mixture of phenol and chloroform (50:50) and the aqueous layer was recovered. The DNA was recovered from the aqueous layer by the addition of 0.1 volume of 3M sodium acetate and 2.5 volumes of absolute ethanol. The digested DNA was collected by centrifugation, the supernatant was removed and the DNA dried and resuspended in water.

B. Preparation of the TLB Linker

The following single stranded DNA segments are conventionally synthesized by methods well known in the art on an automated DNA synthesizer (Model 380B Applied Biosystems 850 Lincoln Center Drive, Foster City Calif. 94404) using $\beta$-cyanoethyl phosphoramidite chemistry.

BGT3 and BGT4 are complementary DNA molecules. The synthetic DNA segments were dissolved in 50 $\mu l$ of TE buffer (TE is 10 mM Tris-HCl (pH 7.4) and 1 mM ethylenediaminetetraacetic acid (EDTA)) and stored at 0° C.

The DNA strands were annealed as follows. Fifty pmoles each of BGT3 and BGT4 were mixed and heated to 95° C. for 15 minutes. The mixture was slowly brought to room temperature allowing the two complementary strands to anneal and form the double stranded DNA linker known as TLB.

C. Final Construction of pLP53-TLB

The DNA prepared in Example 1A was ligated with TLB (SEQ ID NO: 7). One $\mu l$ of the DNA from Example 1A and 1 $\mu l$ of TLB were ligated in a reaction that contained 1 $\mu l$ (10 units) of T4 DNA ligase, 66 mM Tris-HCl (pH 7.6), 6.6 mM $MgCl_2$, 10 mM dithiothreitol (DTT) and 66 mM adenosine 5'-triphosphate (ATP) in a total volume of 10 $\mu l$. The mixture was incubated at 4° C. for 16 hours. The ligation mix was used to transform *Escherichia coli* K12 AG1 as described below.

D. Transformation Procedure

Frozen competent *Escherichia coli* K12 AG1 cells are obtained from Stratagene, 3770 Tansey Road, San Diego, Calif. 92121. About 5 $\mu l$ of the ligation reaction is mixed with a 100 $\mu l$ aliquot of competent cells and then the cell-DNA mixture is incubated on ice for one hour, heat-shocked at 42° C. for 45 seconds, then chilled on ice for about 2 minutes. The cell-DNA mixture is diluted into 1 ml of SOC media (2% tryptone, 0.05% yeast extract, 10 mM NaCl, 2.5 mM KCl, 10 mM each of $MgCl_2$ and $MgSO_4$, 20 mM glucose and distilled water) in Falcon 2059 tubes (Curtin Matheson, Chicago, Ill.) and incubated at 37° C. for one hour. About one hundred microliter aliquots are plated on LB-agar plates (1% tryptone, 0.5% yeast extract, 1% NaCl and 1.5% agar, pH 7.0) containing 100 $\mu g$/ml ampicillin and incubated at 37° C. until colonies appear.

Alternatively, cells can be made competent for transformation as follows. A 50 ml culture of *E. coli* K12 AG1 cells is grown in L-broth (10 g tryptone, 10 g NaCl and 5 g yeast extract per liter of $H_2O$ and brought to pH 7.5) to an $O.D._{590}$ of 0.5 absorbance units. The culture is chilled on ice for ten minutes and then the cells are collected by centrifugation. The cell pellet is resuspended in 25 ml of cold 50 mM $CaCl_2$:10 mM Tris-HCl (pH 8.0) and incubated on ice for 15 minutes. The cells are collected by centrifugation, the cell pellet is resuspended in 2.5 ml of cold 50 mM $CaCl_2$:10 mM Tris-HCl (pH 8.0) and the sample can be held at 4° C. for 16 hours. The transformation of these competent cells is carried out as described above.

E. DNA Isolation

Following transformation, ampicillin resistant cells were picked and used to inoculate 2 ml of TY broth (1% tryptone, 0.5% yeast extract, 1% NaCl, pH 7.4) and 100 μg/ml ampicillin. These cultures were grown for 16 hours at 37° C. with aeration. Plasmid DNA was isolated from the cultures as follows. All of the following manipulations were done at ambient temperature unless otherwise indicated. One and a half ml of each of the cultures was transferred to a microcentrifuge tube. The cells were collected by a 1 minute centrifugation. The supernatant was removed with a fine-tip aspirator and the cell pellet was suspended in 100 μl of a solution containing 50 mM glucose, 10 mM EDTA and 25 mM Tris-HCl (pH 8.0). After incubation at room temperature for 5 minutes, 200 μl of an alkaline sodium dodecyl sulfate (SDS) solution (0.2N NaOH, 1% SDS) was added. The tube was gently inverted to mix and then maintained on ice for 5 minutes. Next, 150 μl of a potassium acetate solution (prepared by adding 11.5 ml of glacial acetic acid and 28.5 ml of water to 60 ml of 5M potassium acetate, resulting in a solution which is 3M with respect to potassium and 5M with respect to acetate) was added and the contents of the tube mixed by gently vortexing. The sample was kept on ice for 5 minutes and then centrifuged for 10 minutes. The supernatant was transferred to a second centrifuge tube to which an equal volume of a mixture of phenol (saturated with 0.1M Tris (pH 8.0)) and chloroform was added. The sample was mixed and then centrifuged for 5 minutes. The supernatant was collected. One ml of ice-cold absolute ethanol was added to the supernatant. The sample was mixed, held at room temperature for 5 minutes, and then the DNA was collected by a 5 minute centrifugation. The supernatant was removed by aspiration, and 500 μl of 70% ethanol was added to the DNA pellet. The sample was gently vortexed to wash the pellet and centrifuged for 2 minutes. The supernatant was removed and the DNA pellet was dried under vacuum. The DNA was dissolved in 50 μl of TE buffer and stored at 4° C.

Figure 2:
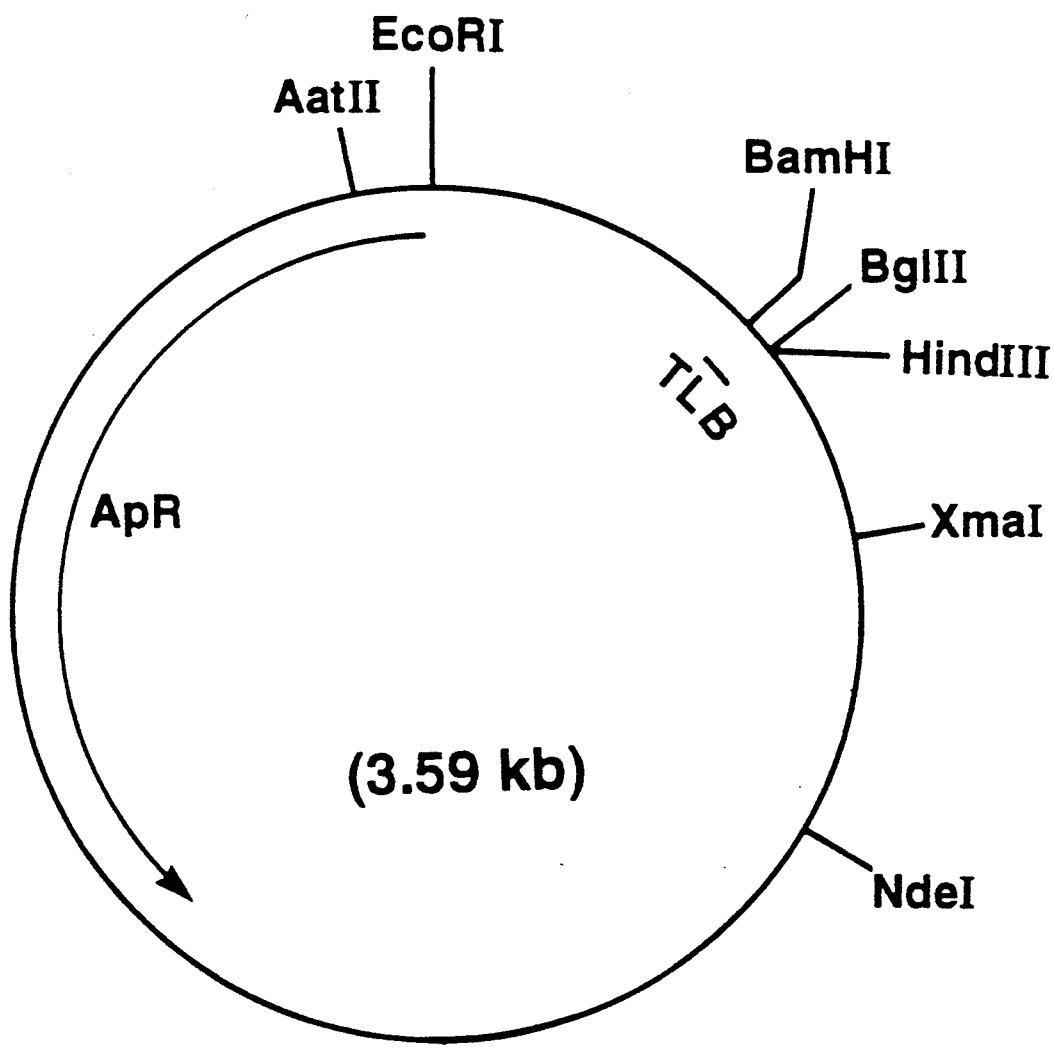
FIG. 2 is a restriction and function map of pLP53-TLB.

A restriction and function map of pLP53-TLB is shown in FIG. 2.

F. Large Scale Plasmid DNA Isolation

Large scale isolation of plasmid DNA can be carried out by the following procedure.

A small portion of an overnight culture of *Escherichia coli* K12 AG1/pLP53-TLB is spread onto L-agar plates containing 100 μg/ml ampicillin in a manner so as to obtain a single colony isolate. The single colony obtained is inoculated into 10 ml of L-broth containing 100 μg/ml ampicillin and incubated overnight at 37° C. with vigorous shaking. The 10 ml overnight culture is inoculated into 500 ml L-broth containing 100 μg/ml ampicillin and incubated at 37° C. with vigorous shaking until the culture reached stationary phase.

The following procedure is adapted from Maniatis et al., 1982, *Molecular Cloning* (Cold Spring Harbor Laboratory).

The cells are harvested by centrifugation at 4000Xg for 10 minutes at 4° C., and the supernatant is discarded. The cell pellet is washed in 100 ml of ice-cold STE buffer (0.1M NaCl; 10 mM Tris-HCl, pH 7.8; and 1 mM EDTA). After washing, the cell pellet is resuspended in 10 ml of Solution 1 (50 mM glucose; 25 mM Tris-HCl, pH 8.0; and 10 mM EDTA) containing 5 μg/ml lysozyme and left at room temperature for 10 minutes. Twenty ml of Solution 2 (0.2N NaOH and 1% SDS) are then added to the lysozyme-treated cells, and the solution is gently mixed by inversion. The mixture is incubated on ice for 10 minutes.

Fifteen ml of ice-cold 5M potassium acetate, pH 4.8, are added to the lysed-cell mixture and the solution mixed by inversion. The solution is incubated on ice for 10 minutes. The 5M potassium acetate solution is prepared by adding 11.5 ml of glacial acetic acid to 28.5 ml of water and 60 ml of 5M potassium acetate; the resulting solution is 3M with respect to potassium and 5M with respect to acetate.

The lysed cell mixture is centrifuged in a Beckman SW27 centrifuge (or its equivalent) at 20,000 rpm for 20 minutes at 4° C. The cell DNA and debris formed a pellet on the bottom of the tube. About 36 ml of supernatant are recovered, and 0.6 volumes of isopropanol are added, mixed, and the resulting solution left at room temperature for 15 minutes. The plasmid DNA is collected by centrifugation at 12,000 g for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of cesium chloride (CsCl) are added to the DNA solution. About 0.8 ml of a 10 μg/ml solution of ethidium bromide in water is added for each 10 ml of CsCl-DNA solution. The final density of the solution is about 1.55 g/ml, and the ethidium bromide concentraton is about 600 μg/ml. The solution is transferred to a Beckman Type 50 centrifuge tube, filled to the top with paraffin oil, sealed, and centrifuged at 45,000 rpm for 24 hours at 20° C. After centrifugation, two bands of DNA are visible in ordinary light. After removing the cap from the tube, the lower DNA band is removed by using a syringe with a #21 hypodermic needle inserted through the side of the centrifuge tube.

The ethidium bromide is removed by several extractions with water-saturated 1-butanol. The CsCl is removed by dialysis against TE buffer. After extractions with buffered phenol and then chloroform, the DNA is precipitated, washed with 70% ethanol, and dried.

Example 2

Construction of pmt6-hd

A. Construction of Intermediate Plasmid pTPA103

Figure 3:
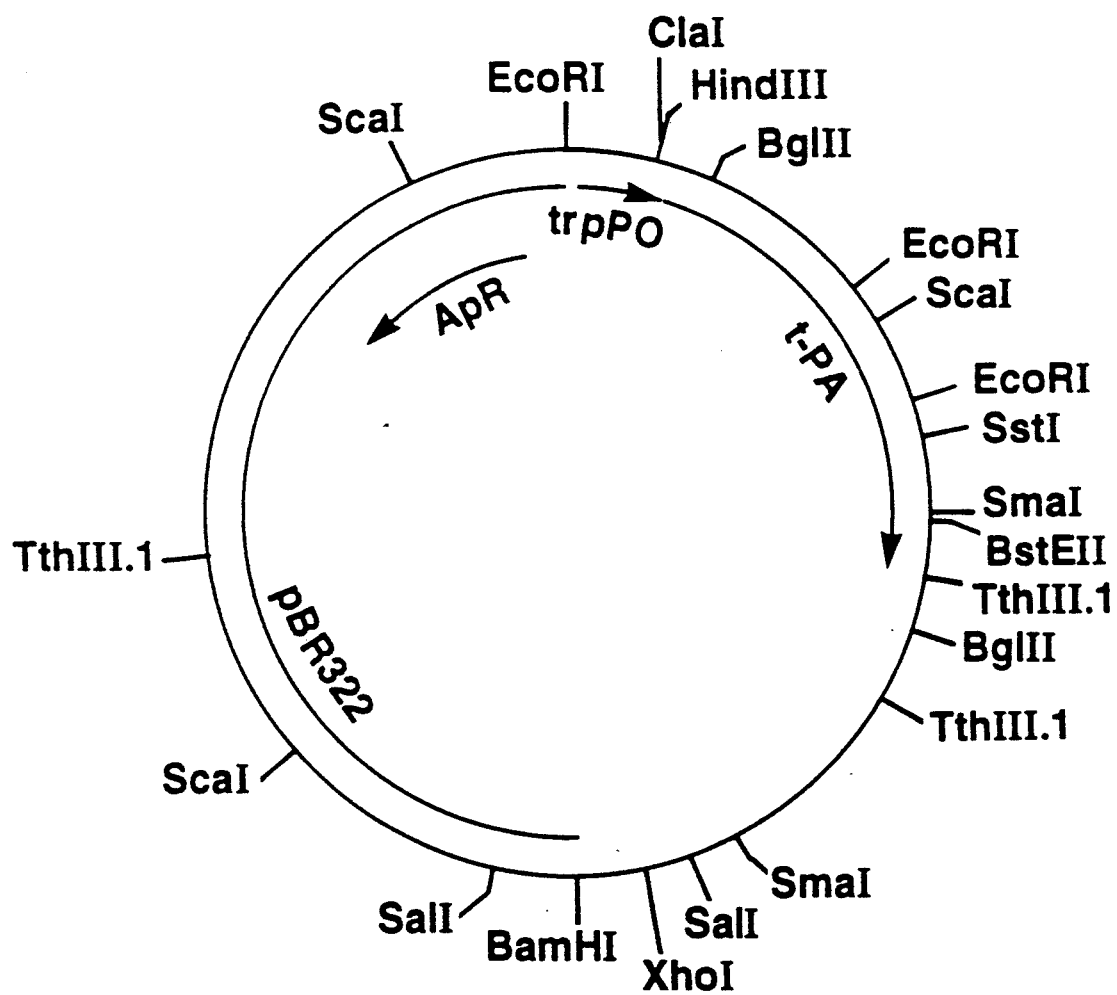
FIG. 3 is a restriction and function map of pTPA102.

Plasmid pTPA102 comprises the coding sequence of human tissue plasminogen activator. Plasmid pTPA102 can be isolated from *Escherichia coli* K12 MM294/pTPA102, a strain available from the Northern Regional Research Laboratory under the accession number NRRL B-15834. A restriction site and function map of plasmid pTPA102 is presented in FIG. 3 of the accompanying drawings. Plasmid pTPA102 DNA is isolated from *E. coli* K12 MM294/pTPA102 in substantial accordance with the procedure of Example 1F.

Fifty μg of plasmid pTPA102 (in about 50 μl of TE buffer) was added to 10 μl of 10X Tth111I buffer (0.5M NaCl, 80 mM Tris-HCl (pH 7.4), 80 mM MgCl$_2$, 80 mM 2-mercaptoethanol and 1 mg/ml BSA (bovine serum albumin)) and 80 μl of H$_2$O. Ten μl (~50 units) of restriction enzyme Tth111I was added to the solution of DNA, and the resulting reaction was incubated at 65° C. for 2 hours. Following the incubation period, loading buffer was added to the sample (final concentration of loading buffer was 2.5% v/v glycerol, 0.005% w/v bromphenol blue, and 0.05% v/v xylene cyanole). The sample was fractionated by gel electrophoresis through an agarose gel. Following electrophoresis, the gel was strained with a dilute solution of ethidium bromide. The digested DNA was visualized under a 300 nm UV light, and the ~4.4 kb Tth111I restriction fragment that comprises the t-PA coding sequence was isolated from the gel. Methods for preparative gel electrophoresis are known in the art. A number of these methods are described by Maniatis et al., *Molecular Cloning: A Laboratory Manual*, Cold Spring Harbor, N.Y. (2d ed. 1989), and are useful as guides in carrying out the above procedures. About 10 μg of the desired ~4.4 kb Tth111I restriction fragment was obtained and suspended in 10 μl of TE buffer.

About 5 μl of 10X Klenow buffer (500 mM potassium phosphate (pH 7.5), 30 mM MgCl2 and 10 mM 2-mercaptoethanol) and 30 μl of H2O were added to the solution comprising the ~4.4 kb Tth111I restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10X ligase buffer (660 mM Tris-HCl (pH 7.6), 66 mM MgCl2, 100 mM DTT, and 10 mM ATP) and 14 μl of H2O.

BamHI linkers (available from N.E.B.) which had the following sequence:

were kinased and prepared for ligation by the following procedure. Four μl of the BamHI linkers (~2 μg) were dissolved in 20.15 μl of H2O and 5 μl of 10X kinase buffer (500 mM Tris-HCl (pH 7.6) and 100 mM MgCl2), incubated at 90° C. for two minutes, and then cooled to room temperature. Five μl of γ-$^{32}$P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb Tth111I restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 μl of 10X HindIII buffer (500 mM Tris-HCl (pH 8.0), 100 mM MgCl2 and 500 mM NaCl) and 40 μl of H2O. About 5 μl (~50 units) of restriction enzyme HindIII was added to the solution of DNA, and the resulting reaction was incubated at 37° C. for 2 hours.

The HindIII-digested DNA was extracted and then precipitated with ethanol and collected as described in Example 1A, and resuspended in 10 μl of 10X BamHI buffer (500 mM Tris-HCl (pH 8.0), 100 mM MgCl2, 1M NaCl) and 90 μl of H2O. About 10 μl (~100 units) of restriction enzyme BamHI was added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel as described above. About 4 μg of the desired fragment were obtained and suspended in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the *Escherichia coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102. Plasmid pKC7 and plasmid pTPA102 DNA can be obtained from the aforementioned cell lines in substantial accordance with the procedure of Example 1F. This ~0.29 kb EcoRI-ClaI restriction fragment of plasmid pTPA102 comprises the transcription activating sequence and most of the translation activating sequence of the *Escherichia coli* trp gene and has the sequence (SEQ ID NO: 11) depicted below:

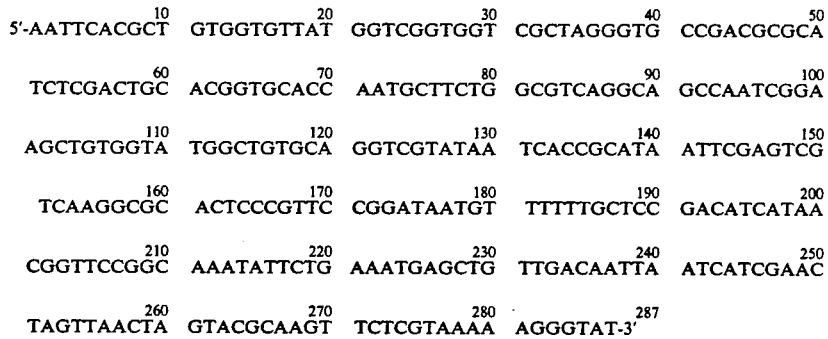

Due to the complementary nature of DNA, the opposite strand of this double stranded DNA compound can be deduced.

Thus, to construct plasmid pRC, about 2 μg of plasmid pKC7 in 10 μl of TE buffer were added to 2 μl of 10X ClaI buffer (0.5M NaCl, 60 mM Tris-HCl (pH 7.9), 60 mM MgCl2, and 1 mg/ml BSA) and 6 μl of H2O. About 2 ul (~10 units) of restriction enzyme ClaI were added to the solution of plasmid pKC7 DNA, and the resulting reaction was incubated at 37° C. for 2 hours. The ClaI-digested plasmid pKC7 DNA was purified and collected by ethanol precipitation. The DNA was resuspended in 2 μl of 10X EcoRI buffer (500 mM Tris-HCl (pH 8.0), 100 mM MgCl₂ and 1M NaCl) and 16 μl of H₂O. About 2 μl (~10 units) of restriction enzyme EcoRI were added to the solution of ClaI-digested plasmid pKC7 DNA, and the resulting reaction was incubated at 37° C. for 2 hours. The EcoRI-ClaI-digested plasmid pKC7 DNA was extracted, precipitated with ethanol and resuspended in 3 μl of 10X ligase buffer and 20 μl of H₂O. A restriction site and function map of plasmid pKC7 can be obtained from Maniatis et al., *Molecular Cloning* (Cold Spring Harbor Laboratory, 1982), page 8.

About 20 μg of plasmid pTPA102 in about 20 μl of TE buffer were added to 10 μl of 10X ClaI buffer and 60 μl of H₂O. About 10 μl (~50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10X EcoRI buffer and 80 μl of H₂O. About 10 μl (~50 units) of restriction enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel (methods for preparative acrylamide gel electrophoresis are described by Maniatis et al., supra); about 1 μg of the desired fragment was obtained, suspended in 5 μl of TE buffer, and added to the solution of EcoRI-ClaI-digested plasmid pKC7 DNA prepared as described above. About 2 μl (~1000 units) of T4 DNA ligase was then added to the mixture of DNA, and the resulting ligation reaction was incubated at 16° C. for 2 hours. The ligated DNA constituted the desired plasmid pRC DNA.

The ligated DNA was used to transform *Escherichia coli* K12 HB101 competent cells (available from BRL) in substantial accordance with the procedure of Example 1D. The transformed cells were plated on L agar containing 100 μg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 1F.

About 2 μg of plasmid pRC DNA in 2 μl of TE buffer were added to 2 μl of 10X HindIII buffer and 16 μl of H₂O. About 2 μl (~10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10X BamHI buffer and 16 μl of H₂O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10X ligase buffer and 20 μl of H₂O. The ~4 μg (in ~5 ul of TE buffer) of ~2.0 kb HindIII-BamHI restriction fragment of plasmid pTPA102 were then added to the solution of BamHI-HindIII-digested plasmid pRC DNA. About 2 μl (~1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms *Escherichia coli* at a lower frequency than closed, circular DNA. To digest the ligated DNA, the DNA was first precipitated with ethanol and then resuspended in 2 μl of 10X NcoI buffer (1.5M NaCl, 60 mM Tris-HCl (pH 7.8), 60 mM MgCl₂, and 1 mg/ml BSA) and 16 μl of H₂O. About 2 μl (~10 units) of restriction enzyme NcoI were added to the solution of DNA, and the resulting reaction was incubated at 37° C. for 2 hours.

Figure 4:
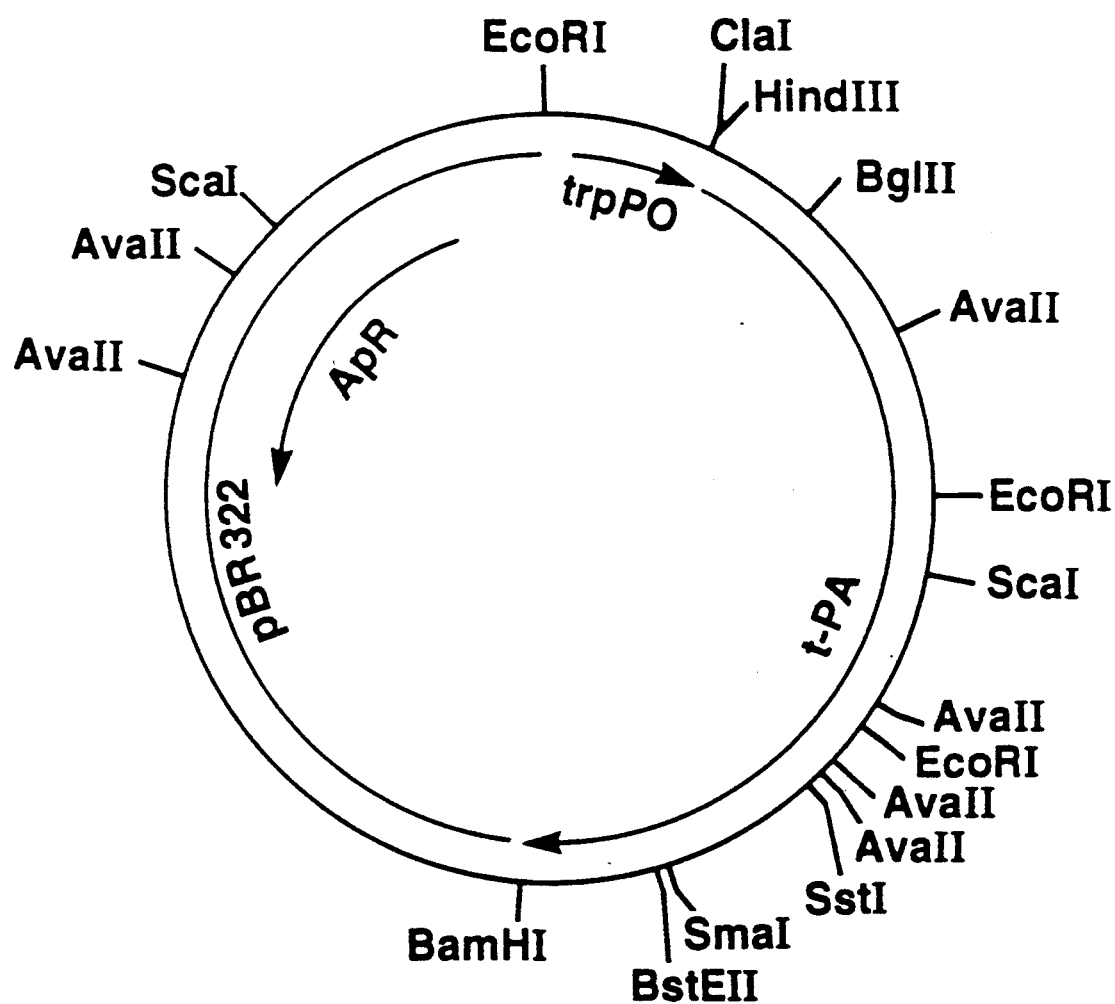
FIG. 4 is a restriction and function map of pTPA103.

The ligated and then NcoI-digested DNA was used to transform *Escherichia coli* K12 RV308 (NRRL B-15624). *Escherichia coli* K12 RV308 cells were made competent and transformed in substantial accordance with the procedure of Example 1D. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the *E. coli* K12 RV308/pTPA103 transformants. A restriction site and function map of plasmid pTPA103 is presented in FIG. 4 of the accompanying drawings. Plasmid pTPA103 DNA was isolated from the *E. coli* K12 RV308/pTPA103 cells in substantial accordance with the procedure of Example 1F.

B. Construction of Intermediate Plasmid pTPA602

About 50 μg of plasmid pTPA103 in 45 μl of glass-distilled H₂O was added to 30 μl of 10X EcoRI buffer and 225 μl of H₂O. About 10 μl (~80 units) of restriction enzyme EcoRI was added to the solution of plasmid pTPA103 DNA, and the mixture was incubated at 37° C. for 90 minutes. The EcoRI-digested plasmid pTPA103 DNA was precipitated with ethanol, resuspended in 50 ul of 1X loading buffer (10% glycerol and 0.02% bromophenol blue), loaded onto an agarose gel, and electrophoresed until the ~1.1 kb EcoRI restriction fragment was separated from the other reaction products. The ~1.1 kb EcoRI restriction fragment that comprises the t-PA amino-terminal-encoding DNA and was isolated from the gel and resuspended in 160 μl of H₂O.

About 40 μl of 10X HgaI buffer (0.5M NaCl, 60 mM Tris-HCl (pH 7.4) and 0.1M MgCl₂), 200 μl of glass-distilled H₂O, and 20 μl (about 10 units) of restriction enzyme HgaI were added to the solution of ~1.1 kb EcoRI restriction fragment, and the resulting reaction was incubated at 37° C. for 4 hours. The HgaI-digested DNA was precipitated with ethanol and then electrophoresed on a 5% acrylamide gel, and the ~520 bp restriction fragment that encodes the amino terminus of TPA was isolated from the gel. About 5 μg of the ~520 bp HgaI fragment was obtained and suspended in 50 μl of H₂O.

About 12.5 μl of 10X Klenow buffer (0.5M Tris-HCl (pH 7.4), and 0.1M MgCl₂), 2 μl of a solution that was 6.25 mM in each of the four deoxynucleotide triphosphates, 2 μl of 0.2M DTT, 1 μl of 7 μg/ml BSA, 57.5 μl of glass-distilled H₂O, and 2 μl (~10 units) of Klenow enzyme were added to the solution of the ~520 bp HgaI restriction fragment, and the resulting reaction was incubated at 20° C. for 30 minutes. The Klenow-treated DNA was incubated at 70° C. for 15 minutes and precipitated with ethanol.

About 500 picomoles of BamHI linker were phosphorylated using polynucleotide kinase in a total reaction volume of 25 μl. The reaction was carried out in substantial accordance with the procedure described in Example 2A. The kinased BamHI linkers were added to the solution of Klenow-treated, ~520 bp HgaI restriction fragment together with 15 μl of 10X ligase buffer, 7 μl (~7 Weiss units) of T4 DNA ligase, and enough glass-distilled H₂O to bring the reaction volume to 150 μl. The resulting reaction was incubated at 16° C. overnight.

The ligation reaction was heat-inactivated, and the DNA was precipitated with ethanol and resuspended in 5 μl of 10X BamHI buffer and 45 μl of H₂O. About 1 μl (~16 units) of restriction enzyme BamHI was added to the solution of DNA, and the resulting reaction was incubated at 37° C. for 90 minutes. Then, another 16 units of BamHI enzyme were added to the reaction mixture, and the reaction was incubated at 37° C. for another 90 minutes. The reaction mixture was then electrophoresed on a 5% polyacrylamide gel, and the ~530 bp HgaI restriction fragment, now with BamHI ends, was purified from the gel. About 2 μg of the desired fragment was obtained and suspended in 20 μl of H₂O.

Figure 5:
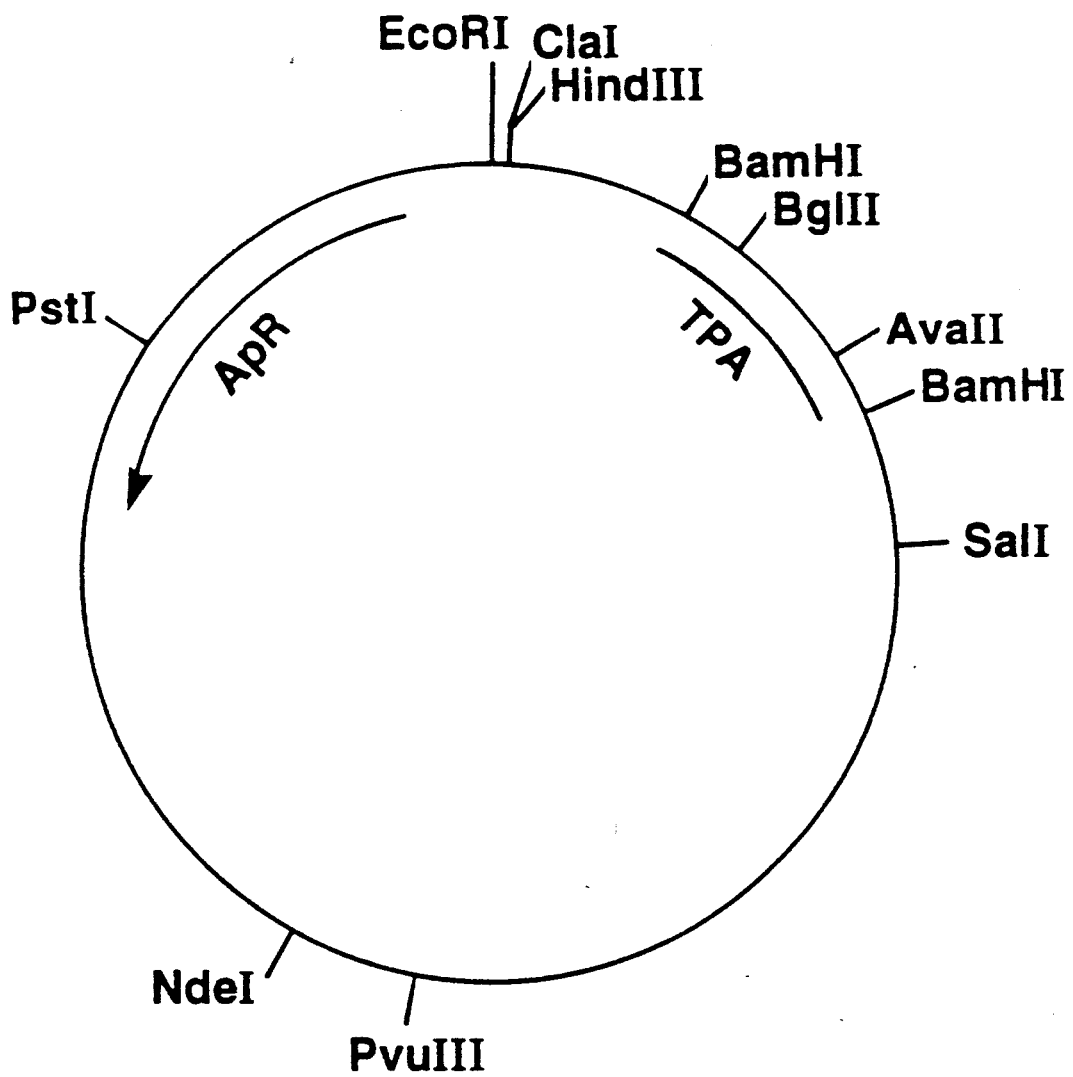
FIG. 5 is a restriction and function map of pTPA602.

BamHI-digested, dephosphorylated plasmid pBR322 DNA can be obtained from New England Biolabs. About 0.1 μg of BamHI-digested, dephosphorylated plasmid pBR322 in 2 μl of H₂O was added to 1 μl of the ~530 bp HgaI restriction fragment, with BamHI ends, of plasmid pTPA103, 14 μl of H₂O, 2 μl of 10X T4 DNA ligase buffer, and 1 μl (~1 Weiss unit) of T4 DNA ligase, and the resulting reaction was incubated at 16° C. overnight. The ligated DNA constituted the desired plasmid pTPA602 and an equivalent plasmid designated pTPA601, which differs from plasmid pTPA602 only with respect to the orientation of the inserted, ~530 bp restriction fragment. A restriction site and function map of plasmid pTPA602 is presented in FIG. 5 of the accompanying drawings.

The ligated DNA was used to transform *Escherichia coli* K12 MM294 (NRRL B-15625) in substantial accordance with the procedure of Example 1D. The transformed cells were plated on L agar containing ampicillin, and the ampicillin-resistant *E. coli* K12 MM294/pTPA602 and *E. coli* K12 MM294/pTPA601 cells were identified by restriction enzyme analysis of their plasmid DNA. Presence of an ~530 bp BamHI restriction fragment indicated that the plasmid was either pTPA602 or plasmid pTPA601.

C. Construction of Intermediate Plasmid pTPA603

About 5 μg of plasmid pTPA602 was dissolved in 20 μl of 10X BglII buffer (500 mM Tris-HCl (pH 8.0), 100 mM MgCl₂, 1M NaCl) and 180 μl of H₂O. About 3 μl (~24 units) of restriction enzyme BglII were added to the solution of plasmid pTPA602 DNA, and the resulting reaction was incubated at 37° C. for 90 minutes. Then, ~13 μl of 10X BamHI buffer was added to the reaction mixture to bring the salt concentration of the reaction mixture up to that recommended for SalI digestion, and 2 μl (~20 units) of restriction enzyme SalI was added to the reaction. The reaction was incubated at 37° C. for another 2 hours; then, the DNA was precipitated with ethanol, resuspended in 75 μl of 1X loading buffer, loaded onto an agarose gel, and electrophoresed until the ~4.2 kb BglII-SalI restriction fragment was separated from the other digestion products. The region of the gel containing the ~4.2 kb BglII-SalI restriction fragment was excised from the gel, frozen, and the frozen segment was wrapped in plastic and squeezed to remove the ~4.2 kb fragment. The DNA was precipitated and resuspended in 20 μl of H₂O; about 200 nanograms of the desired fragment were obtained.

About 12 μg of plasmid pTPA103 was dissolved in 15 μl of 10X BglII buffer and 135 μl of H₂O. About 2 μl (~16 units) of restriction enzyme BglII was added to the solution of plasmid pTPA103 DNA, and the resulting reaction was incubated at 37° C. for 90 minutes. About 10 μl of 10X BamHI buffer was added to the solution of BglII-digested plasmid pTPA103 DNA to bring the salt concentration of the reaction mixture up to that required for SalI digestion. Then, about 2 μl (~20 units) of restriction enzyme SalI was added to the solution of BglII-digested plasmid pTPA103 DNA, and the reaction was incubated at 37° C. for another 90 minutes. The BglII-SalI digested plasmid pTPA103 DNA was concentrated by ethanol precipitation and then loaded onto an agarose gel, and the ~2.05 kb BglII-SalI restriction fragment that encodes all but the amino-terminus of t-PA was isolated from the gel, precipitated with ethanol and resuspended in 20 μl of H₂O. About 2 μg of the desired fragment was obtained.

Figure 6:
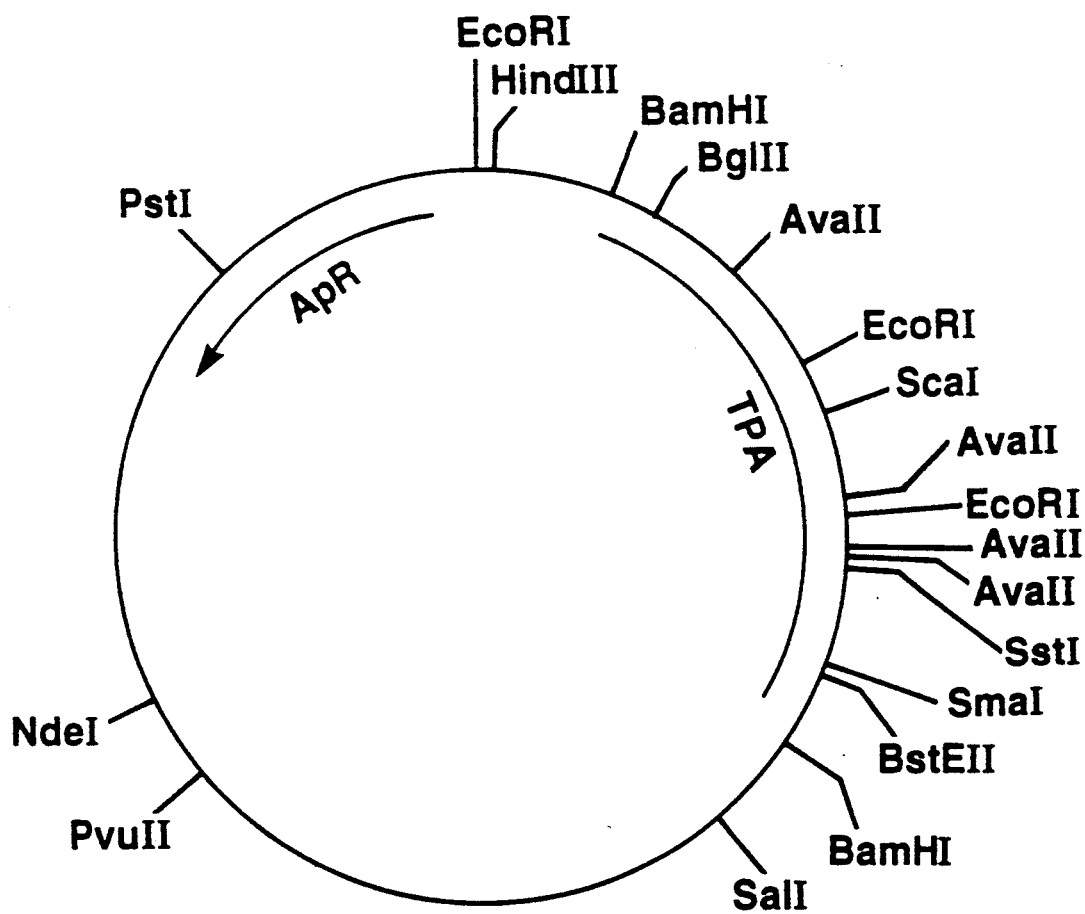
FIG. 6 is a restriction and function map of pTPA603.

About 5 μl of the ~4.2 kb BglII-SalI restriction fragment of plasmid pTPA602 and 2 μl of the ~2.05 kb BglII-SalI restriction fragment of plasmid pTPA103 were added to 2 μl of 10X ligase buffer, 10 μl of H₂O, and 1 μl (~1 Weiss unit) of T4 DNA ligase, and the resulting ligation reaction was incubated at 16° C. overnight. The ligated DNA constituted the desired plasmid pTPA603. A restriction site and function map of plasmid pTPA603 is presented in FIG. 6 of the accompanying drawings.

The ligated DNA was used to transform *Escherichia coli* K12 MM294 in substantial accordance with the procedure of Example 1D. The transformed cells were plated on L agar containing ampicillin, and the ampicillin-resistant *E. coli* K12 MM294/pTPA603 transformants were identified by restriction enzyme analysis of their plasmid DNA.

D. Final Construction of Plasmid pmt6-hd

Site specific mutagenesis of the TPA coding region and the construction of plasmid pmt6-hd is accomplished as follows. About 5 μg of plasmid pTPA103 in 10 μl of dH₂O are added to about 10 μl of 10X HindIII buffer and 80 μl of dH₂O. One μl (20 units) of restriction enzyme HindIII is added to the solution of plasmid pTPA103 DNA, and the resulting reaction is incubated at 37° C. for 90 minutes. One μl (20 units) of restriction enzyme SstI and 10 μl of 1M Tris-HCl (pH 7.6) is added to the solution of HindIII-digested plasmid pTPA103 DNA, and the resulting reaction is incubated at 37° C. for 90 minutes. The 1.4 kb HindIII-SstI restriction fragment is isolated by preparative gel electrophoresis.

About 4.5 μg of the replicative form (RF) of M13mp18 DNA (available from NEB) in 35 μl of dH₂O is added to 10 μl of 10X HindIII buffer and 55 μl of dH₂O. One μl (about 20 units) of restriction enzyme HindIII is added to the solution of M13mp18 DNA, and the resulting reaction was incubated at 37° C. for 1 hour. One μl (about 20 units) of restriction enzyme SstI and 10 μl of 1M Tris-HCl (pH 7.6) is added to the solution of HindIII-digested M13mp18 DNA, and the resulting reaction is incubated at 37° C. for 1 hour. The large HindIII-SstI restriction fragment of M13mp18 is obtained by preparative gel electrophoresis and suspended in 20 μl of dH₂O. About 2 μl of the large HindIII-SstI restriction fragment of M13mp18, 2 μl of 10X T4 DNA ligase buffer, 12 μl of dH₂O and ~1 μl (about 1 Weiss unit) of T4 DNA ligase is added to 3 μl of the ~1.4 kb HindIII-SstI restriction fragment of plasmid pTPA103, and the resulting ligation reaction is incubated at 16° C. overnight.

Escherichia coli JM103 cells are made competent and transfected with the ligation mix in substantial accordance with the procedure described in the BRL M13 Cloning/'Dideoxy' Sequencing Instruction Manual, except that the amount of DNA used per transfection is varied (host cells other than JM103 may be used in this procedure. For examples of appropriate host cells, see Maniatis et al, 1989, vol. 1 at pp. 414–415). This method is also described by Maniatis et al., 1989, 1:4.37. Recombinant plaques are identified by insertional inactivation of the β-galactosidase α-fragment-encoding gene, which results in the loss of the ability to cleave X-Gal (5-bromo-4-chloro-3-indolyl-β-D-galactopyranoside) to its indigo colored cleavage product. For screening purposes, several white plaques are picked into 2.5 ml of L broth, to which is added 0.4 ml of E. coli K12 JM103 in logarithmic growth phase, that are cultured in minimal media stock to insure retention of the F episome that carries proAB. The 2.5 ml plaque-containing cell suspensions are incubated in an air-shaker at 37° C. for 8 hours. Cells from 1.5 ml aliquots are pelleted and RF DNA isolated in substantial accordance with the alkaline miniscreen procedure of Example 1E. The remainder of each culture is stored at 4° C. for stock. The desired phage, designated MP18BW47, contains the ~1.4 kb HindIII-SstI restriction fragment of plasmid pTPA103 ligated to the ~7.2 kb EcoRI-HindIII restriction fragment of M13mp18.

About fifty ml of log phase Escherichia coli JM103 are infected with MP18BW47 and incubated in an airshaker at 37° C. for 18 hours. The infected cells are pelleted by low speed centrifugation, and single-stranded MP18BW47 DNA is prepared from the culture supernatant by scaling up the procedure given in the Instruction Manual. Single-stranded MP18BW47 is mutagenized in substantial accordance with the teaching of Adelman, et al., 1983, DNA 2(3): 183–193, except that the Klenow reaction is done at room temperature for 30 minutes, then at 37° C. for 60 minutes, then at 10° C. for 18 hours. In addition, the S1 treatment is done at 20° C., the salt concentration of the buffer is one-half that recommended by the manufacturer, and the M13 sequencing primer (BRL) is used. The synthetic oligodeoxyribonucleotide primer used to delete the coding sequence for amino acid residues 4 through 175 of native TPA is

5'-GGAGCCAGATCTTACCAAGGAAACAGTGACTGCTAC-3'(SEQ ID NO: 12).

The resulting mutagenesis mix is used to transfect Escherichia coli K12 JM103 in substantial accordance with the infection procedure described above. Desired mutants are identified by restriction enzyme analysis of RF DNA and by Maxam and Gilbert DNA sequencing (Maxam, A. M. and Gilbert, W. 1980, Proc. Natl. Acad. Sci. U.S.A. 74:560). The desired mutant, which has the coding sequence for amino acid residues 4 through 175 of native TPA deleted, was designated MP18BW52.

Plasmid pmt6-hd was constructed as follows. First, the plasmid pTPA603 was digested to completion with BamHI in accordance with the methods described above, and the ~1.9 kb BamHI fragment was isolated by preparative gel electrophoresis. Next, plasmid pAc373 (Miyamoto et al., 1985, Mol. Cell. Biol. 5:2860–2865) was digested with BamHI, extracted and ethanol precipitated. The BamHI digested pAc373 DNA was ligated with the ~1.9 kb BamHI fragment from plasmid pTPA603 to create intermediate plasmid pL100. Plasmid pAc373 was used because of the presence of convenient cloning sites in this plasmid. Other plasmids can be used instead of plasmid pAc373 to create plasmid pL100. Examples of such plasmids include pBR322, pUC18, and pUC19, all of which are publicly available. The ligated DNA was used to transform Escherichia coli K12 MM294 in substantial accordance with the procedure of Example 1D. The transformed cells were plated on L agar containing ampicillin, and the ampicillin-resistant E. coli K12 MM294/pL100 transformants were identified by restriction enzyme analysis of their plasmid DNA.

Plasmid pL100 DNA was digested to completion with restriction enzymes BglII and SstI and a 9.7 kb BglII-SstI fragment was isolated by preparative gel electrophoresis. MP18BW52 DNA, obtained as above, was digested with restriction enzymes BglII and SstI and an ~718 bp BglII-SstI fragment was isolated by preparative gel electrophoresis. This fragment was ligated with the 9.7 kb BglII-SstI fragment of plasmid pL100 in accordance with the method of Example 1C to create intermediate plasmid pL229. Plasmid pL229 was used to transform Escherichia coli K12 MM294 in substantial accordance with the procedure of Example 1D. The transformed cells were plated on L agar containing ampicillin, and the ampicillin-resistant E. coli K12 MM294/pL229 transformants were identified by restriction enzyme analysis of their plasmid DNA. Plasmid pL229 DNA was isolated as described in Example 1E and then digested with restriction enzyme BamHI. A ~1.4 kb BamHI fragment was isolated by preparative gel electrophoresis.

Figure 7:
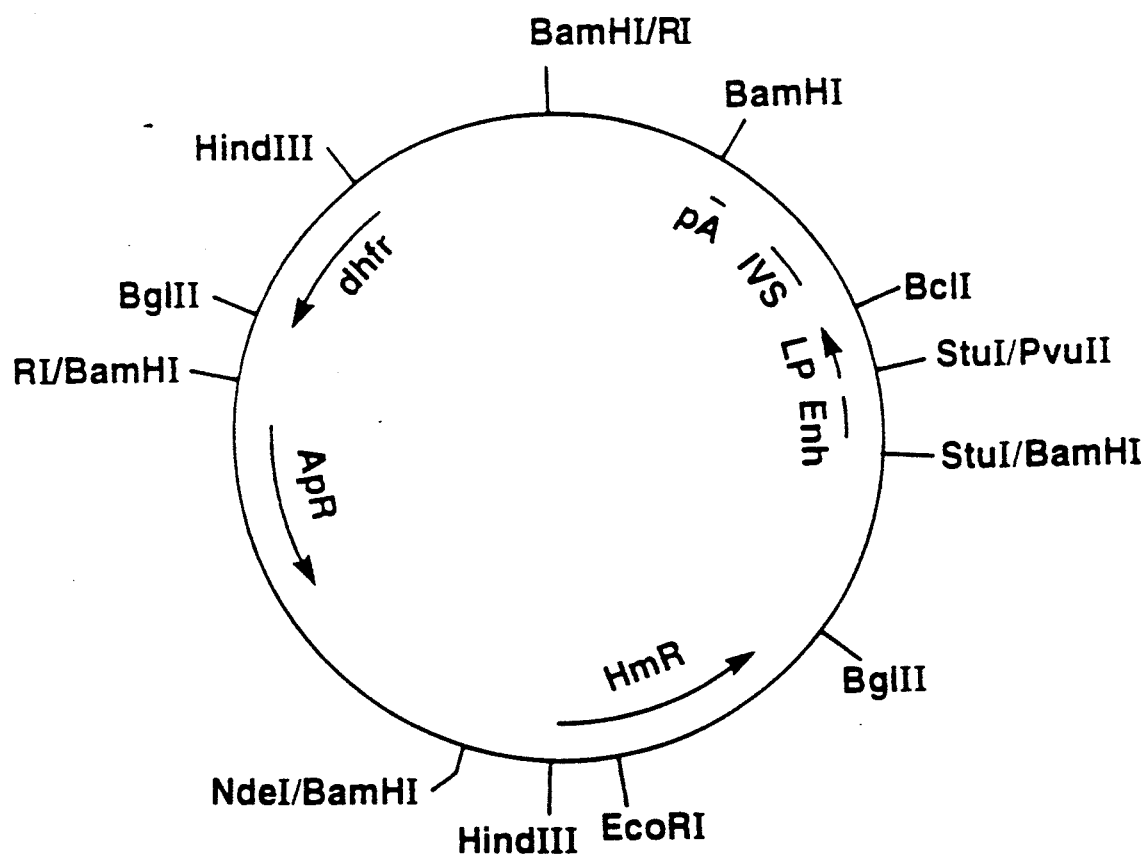
FIG. 7 is a restriction and function map of phd.

Escherichia coli K12 GM48/phd cells are obtained in lyophilized form from the American Type Culture Collection under accession number NRRL B-18525. The lyophilized cells are plated on L-agar plates containing 100 μg/ml ampicillin and incubated at 37° C. to obtain single colony isolates. Plasmid DNA can be isolated from these cells by the method described in Example 1F. A restriction and function map of plasmid phd is presented in FIG. 7. Plasmid phd was digested with BclI, purified and collected by ethanol precipitation. The BclI digested phd DNA was ligated with the ~1.4 kb BamHI fragment of plasmid pL229 to create the desired plasmid pmt6-hd. The ligated DNA was used to transform Escherichia coli K12 MM294 in substantial accordance with the procedure of Example 1D. The transformed cells were plated on L agar containing ampicillin, and the ampicillin-resistant *E. coli* K12 MM294/pmt6-hd transformants were identified by restriction enzyme analysis of their plasmid DNA.

Figure 8:
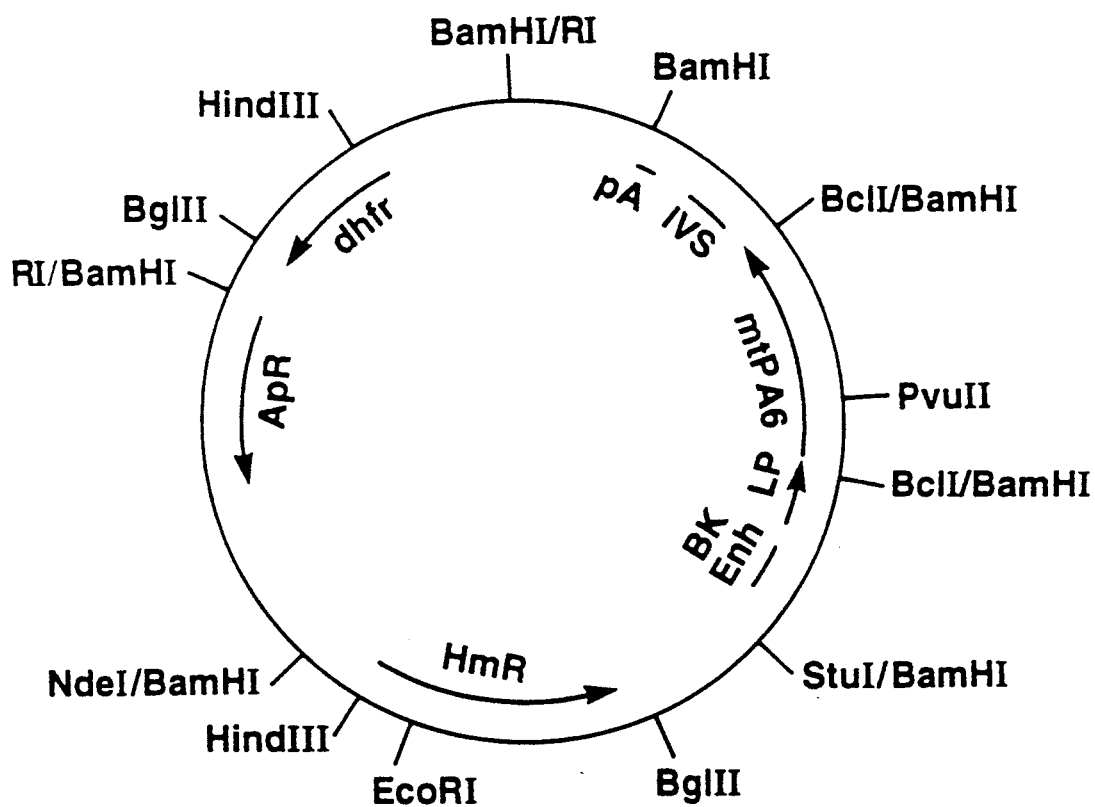
FIG. 8 is a restriction and function map of pmt6-hd.

A restriction and function map of pmt6-hd is shown in FIG. 8.

Example 3

Construction of pTLB-t6

A. Preparation of the 3273 Base Pair BglII-XmaI Restriction Fragment of pLP53-TLB One µg of plasmid pLP53-TLB DNA (prepared in Example 1) was digested to completion with 1 µl (10 units) of BglII and 9 µl (9 units) of XmaI in a 200 µl reaction volume containing 50 mM Tris-HCl (pH 8.0), 10 mM MgCl$_2$, and 50 mM NaCl. The sample was incubated at 37° C. for 2 hours. The digested DNA was purified and collected as described in Example 1A.

B. Preparation of the 1073 Base Pair BglII-XmaI Restriction Fragment of pmt6-hd

Thirty µg of plasmid pmt6-hd DNA (prepared in Example 2) was digested to completion with 2 µl (20 units) of BglII and 25 µl (25 units) of XmaI in a 250 µl reaction volume under the buffer conditions described in Example 3A. Following incubation, 25 µl of loading buffer (25% v/v glycerol, 0.05% w/v bromphenol blue, and 0.5% v/v xylene cyanole) was added to the sample and the digested DNA was fractionated by gel electrophoresis. The 1073 base pair BglII-XmaI restriction fragment was recovered and purified from the gel. The recovered DNA fragment was dissolved in 20 µl of water.

C. Final Construction of pTLB-t6

Fifty nanograms of the 3273 BglII-XmaI restriction fragment of plasmid pLP53-TLB DNA (prepared in Example 3A) was ligated with 0.2 µg of the 1073 base pair BglII-XmaI restriction fragment of plasmid pmt6-hd DNA (prepared in Example 3B) in accordance with the ligation procedure of Example 1C. A portion of the ligation mixture was used to transform competent *Escherichia coli* K12 AG1 cells in accordance with the method described in Example 1D. The transformants were selected on LB agar plates containing 100 µg/ml of ampicillin grown overnight at 37° C. Plasmid DNA was isolated from the ampicillin resistant clones by the DNA isolation procedure of Example 1E. Plasmid pTLB-t6 was identified by restriction enzyme analysis.

Figure 9:
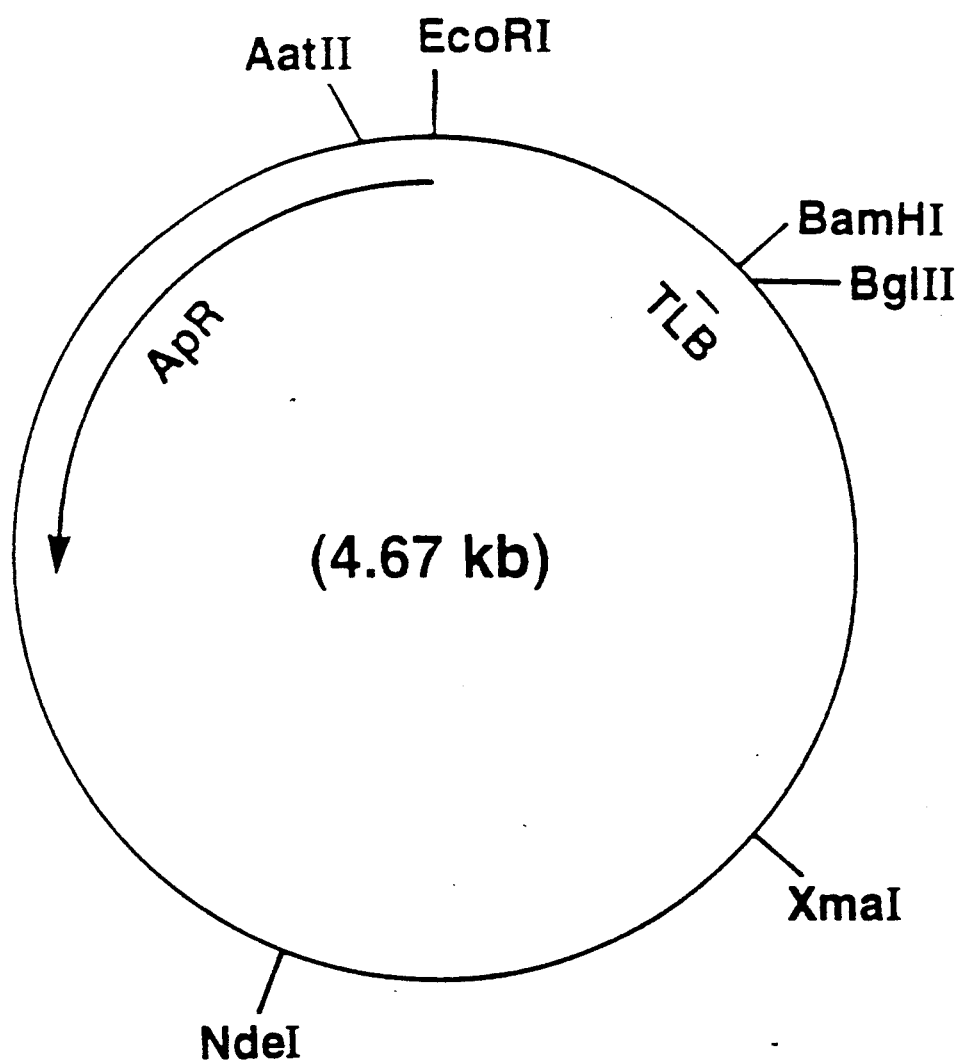
FIG. 9 is a restriction and function map of pTLB-t6.

A restriction site and function map of pTLB-t6 is shown in FIG. 9.

Example 4

Construction of pBKneo1 and pBKneo2

A. Preparation of BK virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M. A. Bioproducts under catalogue number 70-151. Alternatively, BK virus can be propagated in Vero cells (ATCC catalogue number CCL81).

About five 75 mm$^2$ polystyrene flasks comprising confluent monolayers of about $10^6$ PHEK cells are used to prepare the virus. About 1 ml of BK virus at a titer of $10^5$ pfu/ml is added to each flask, which is then incubated at 37° C. for one hour, and then, fresh culture medium (Dulbecco's Modified Eagle's Medium, Gibco, supplemented with 10% fetal bovine serum) is added, and the infected cells are incubated at 37° C. for 10-14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000Xg. The virus in 1 liter of supernatant fluid is precipitated and collected by the addition of 100 g of PEG-6000, incubation of the solution for 24 hours at 4° C., and centrifugation at 5000Xg for 20 minutes. The pellet is dissolved in 0.1X SSC buffer (1XSSC=0.15M NaCl and 0.015M sodium citrate, pH=7) at 1/100th of the original volume. The virus suspension is layered onto a 15 ml solution of saturated KBr in a tube, which is centrifuged at 75,000Xg for 3 hours. Two bands are evident in the KBr solution after centrifugation. The lower band, which contains the complete virion, is collected and desalted on a Sephadex ® G-50 column (Sigma Chemical Co., P.O. Box 14508, St. Louis, Mo. 63178) using TE as an elution buffer.

Sodium dodecyl sulfate (SDS) is added to the solution of purified virions obtained from the column to a concentration of 1%; pronase is added to a concentration of 100 µg/ml, and the solution is incubated at 37° C. for 2 hours. Cesium chloride is then added to the solution to a density of 1.56 g/ml, and ethidium bromide is added to the solution to a final concentration of 100 µg/ml. The solution is centrifuged in a Sorvall (DuPont Inst. Products, Biomedical Division, Newton, Conn. 06470) 865 rotor or similar vertical rotor at 260,000Xg for 24 hours. After centrifugation, the band of virus DNA is isolated and extracted five times with isoamyl alcohol saturated with 100 mM Tris-HCl (pH 7.8). The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000Xg for 10 minutes. The resulting pellet of BK virus DNA is suspended in TE buffer at a concentration of 1 mg/ml.

B. Construction of Plasmids pBKneo1 and pBKneo2

*Escherichia coli* K12 HB101/pdBPV-MMTneo cells are obtained in lyophil form from the American Type Culture Collection under the accession number ATCC 37224. The lyophilized cells are plated on L-agar plates containing 100 µg/ml ampicillin and incubated at 37° C. to obtain single colony isolates. Plasmid DNA can be isolated from these cells in accordance with the plasmid isolation procedure described in Example 1F.

About 5 µg (5 µl) of the plasmid pdBPV-MMTneo DNA prepared above and five µg (5 µl) of the BK virus DNA prepared in Example 4A were each digested at 37° C. for 2 hours in a solution containing 2 µl of 10X BamHI buffer (1.5M NaCl, 60 mM Tris-HCl (pH 7.9), 60 mM MgCl$_2$, and 1 mg/ml BSA), 1 μl of restriction enzyme BamHI, and 7 μl of H$_2$O. The reaction was stopped by an extraction with an equal volume of phenol, followed by two extractions with chloroform. Each BamHI-digested DNA was then precipitated, collected by centrifugation, and resuspended in 5 μl of H$_2$O.

Figure 10:
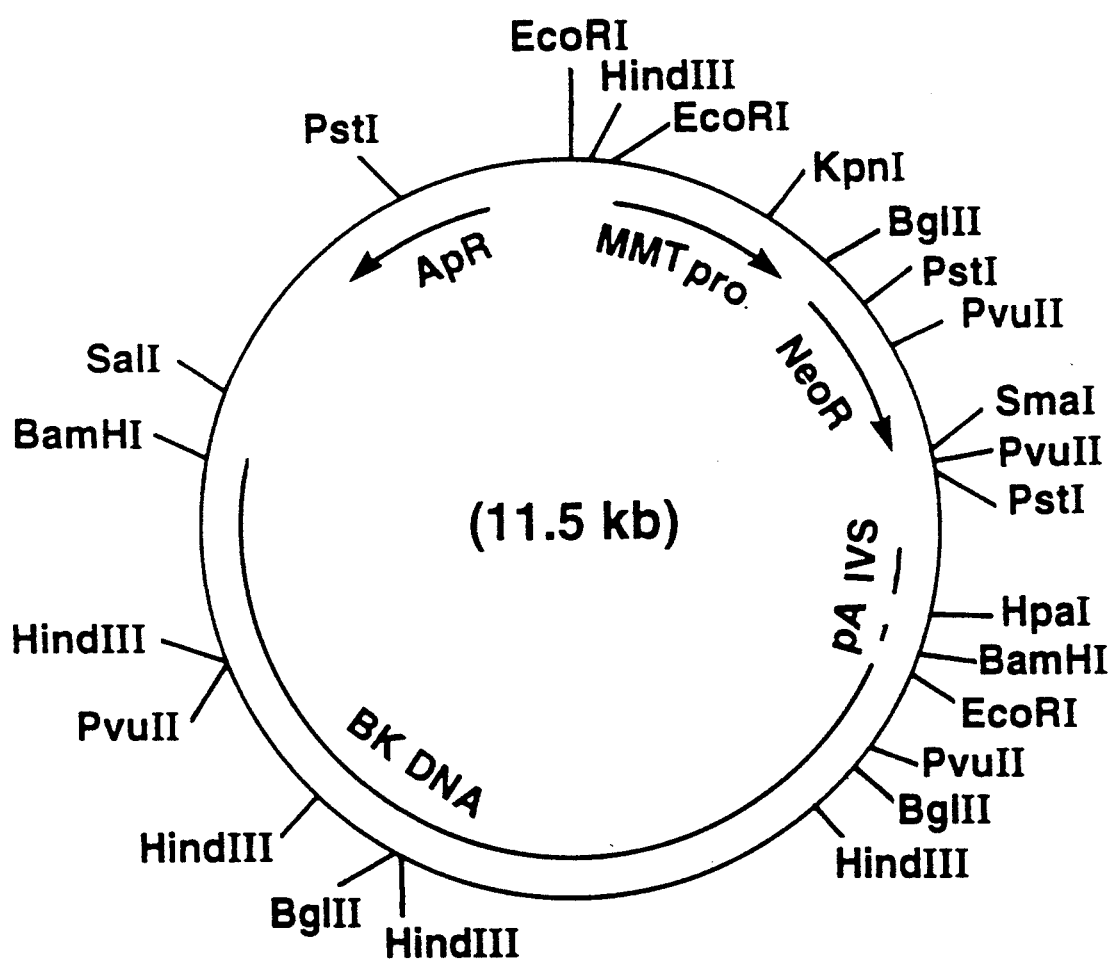
FIG. 10 is a restriction and function map of pBKneo1.

About 1 μl of 10X ligase buffer was added to a mixture of BamHI-digested plasmid pdBPV-MMTneo (1 μl) and BamHI-digested BK virus DNA (1 μl). After 1 μl (~1000 units) of T4 DNA ligase and 6 μl of H$_2$O were added to the mixture of DNA, the resulting reaction was incubated at 16° C. overnight. The ligated DNA constituted the desired plasmids pBKneo1 and pBKneo2, which differ only with respect to the orientation of the BK virus DNA. A restriction site and function map of plasmid pBKneo1 is presented in FIG. 10 of the accompanying drawings.

*Escherichia coli* K12 HB101 cells are available in lyophilized form from the Northern Regional Research Laboratory under the accession number NRRL B-15626. *E. coli* K12 HB101 cells were cultured, made competent for transformation, and transformed with the ligated DNA prepared above in substantial accordance with the procedure of Example 1D. The transformed cells were plated on L-agar plates containing 100 μg/ml ampicillin. *E. coli* K12 HB101/pBKneo1 and *E. coli* K12/pBKneo2 transformants were identified by their ampicillin-resistant phenotype and by restriction enzyme analysis of their plasmid DNA.

Example 5

A. Construction of Intermediate Plasmid pLPcat

The virion DNA of adenovirus 2 (Ad2) is a double-stranded linear molecule about 35.94 kb in size. The Ad2 late promoter can be isolated on an ~0.316 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL) are dissolved in 80 μl of H$_2$O and 10 μl of 10X BalI buffer (100 mM Tris-HCl (pH 7.6), 120 mM MgCl$_2$, 100 mM DTT, and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl, 0.1 mM EDTA, and 20 mM Tris-HCl (pH 8.0)). Next, the membrane is placed in a small tube and immersed in high-salt buffer (1M NaCl, 0.1 mM EDTA, and 20 mM Tris-HCl (pH 8.0)) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25M, and then three volumes of cold, absolute ethanol are added to the solution. The resulting solution is mixed and placed at −70° C. for 10-20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 ug of the desired restriction fragment of Ad2. The purified fragment obtained is dissolved in 10 μl of TE buffer.

About 6 μl of H$_2$O and 2 μl of 10X AccI buffer (60 mM NaCl, 60 mM Tris-HCl (pH 7.5), 60 mM MgCl$_2$, 60 mM DTT, and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H$_2$O and 2 μl of 10X PvuII buffer (600 mM NaCl, 60 mM Tris-HCl (pH 7.5), 60 mM MgCl$_2$, 60 mM DTT, and 1 mg/ml BSA). After the addition of about 2 μl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH$_4$OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H$_2$O.

About 0.25 μg (in 0.5 ul) of BclI linkers (5′-CTGAT-CAG-3′, available from NEB), which had been kinased in substantial accordance with the procedure described in Example 2 was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

Figure 11:
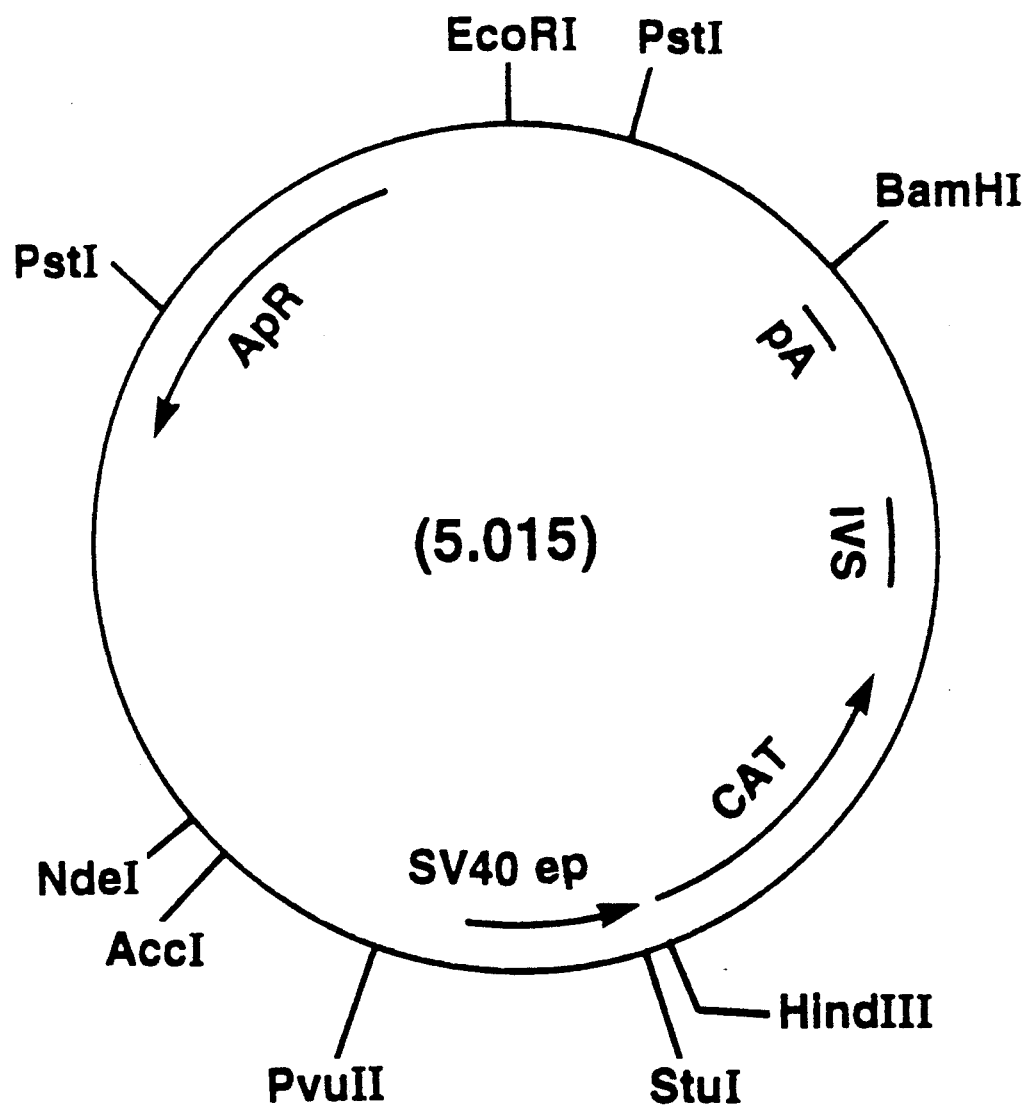
FIG. 11 is a restriction and function map of pSV2cat.

*Escherichia coli* K12 HB101/pSV2cat cells are obtained in lyophilized form from the ATCC under the accession number ATCC 37155, and plasmid pSV2cat DNA was isolated from the cells in substantial accordance with the procedure of Example 1F. A restriction site and function map of plasmid pSV2cat is presented in FIG. 11 of the accompanying drawings. About 1 mg of plasmid pSV2cat DNA is obtained and dissolved in 1 ml of TE buffer. About 3 μg (3 μl) of the plasmid pSV2cat DNA were added to 2 μl of 10X AccI buffer and 16 μl of $H_2O$, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 μl of 10X StuI buffer (1.0M NaCl, 100 mM Tris-HCl (pH 8.0), 100 mM $MgCl_2$, 60 mM DTT, and 1 mg/ml BSA), 5 μl of $H_2O$, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

Figure 12:
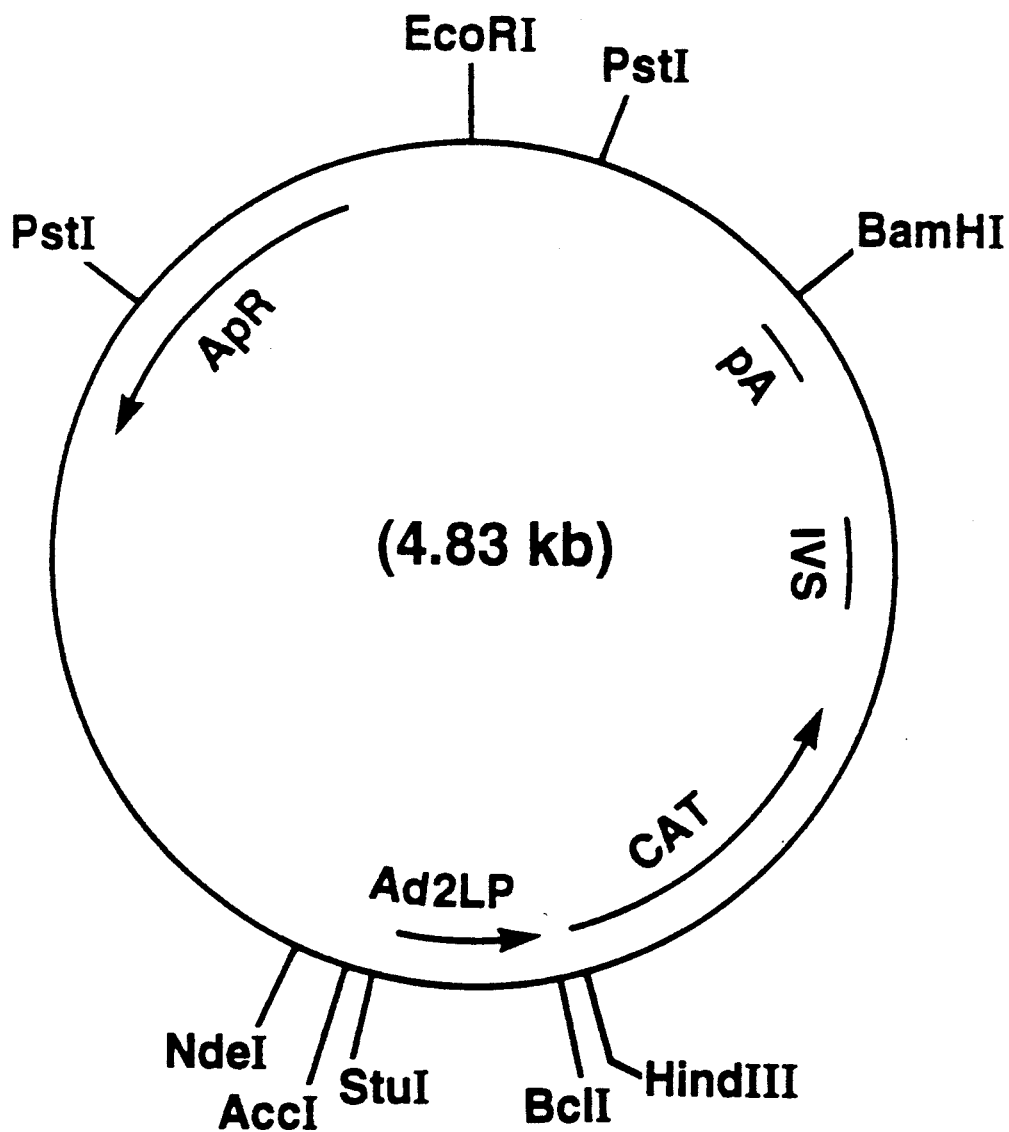
FIG. 12 is a restriction and function map of pLPcat.

About 4 μl of the AccI-StuI-digested plasmid pSV2cat DNA were mixed with about 7 μl of the ~0.32 kb AccI-PvuII (with BclI linkers attached) restriction fragment of Ad2, and after the addition of 3 μl of 10X ligase buffer, 15 μl of $H_2O$, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 12 of the accompanying drawings.

The ligated DNA was used to transform *Escherichia coli* K12 HB101 cells in substantial accordance with the procedure of Example 1D. The transformed cells were plated on L agar containing 50 μg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 1F.

B. Construction of Plasmid pBLcat

About 88 μg of plasmid pBKneo1 DNA (from Example 4B) in 50 μl of TE buffer were added to 7.5 μl of 10X AccI buffer, 30 μl of $H_2O$, and 15 μl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated from the gel. About 5 μg of the fragment were resuspended in 5 μl of 10X PvuII buffer, 45 μl of $H_2O$, and 5 μl (about 25 units) of restriction enzyme PvuII, and the resulting reaction was incubated at 37° C. for 2 hours. The PvuII-digested DNA was then purified and precipitated with ethanol. About 2 μg of the desired ~1.28 kb AccI-PvuII fragment were obtained and dissolved in 5 μl of TE buffer.

About 1 μg of plasmid pLPcat DNA was dissolved in 5 μl of 10X AccI buffer and 40 μl of $H_2O$. About 5 μl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10X StuI buffer, 40 μl of $H_2O$, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

Figure 13:
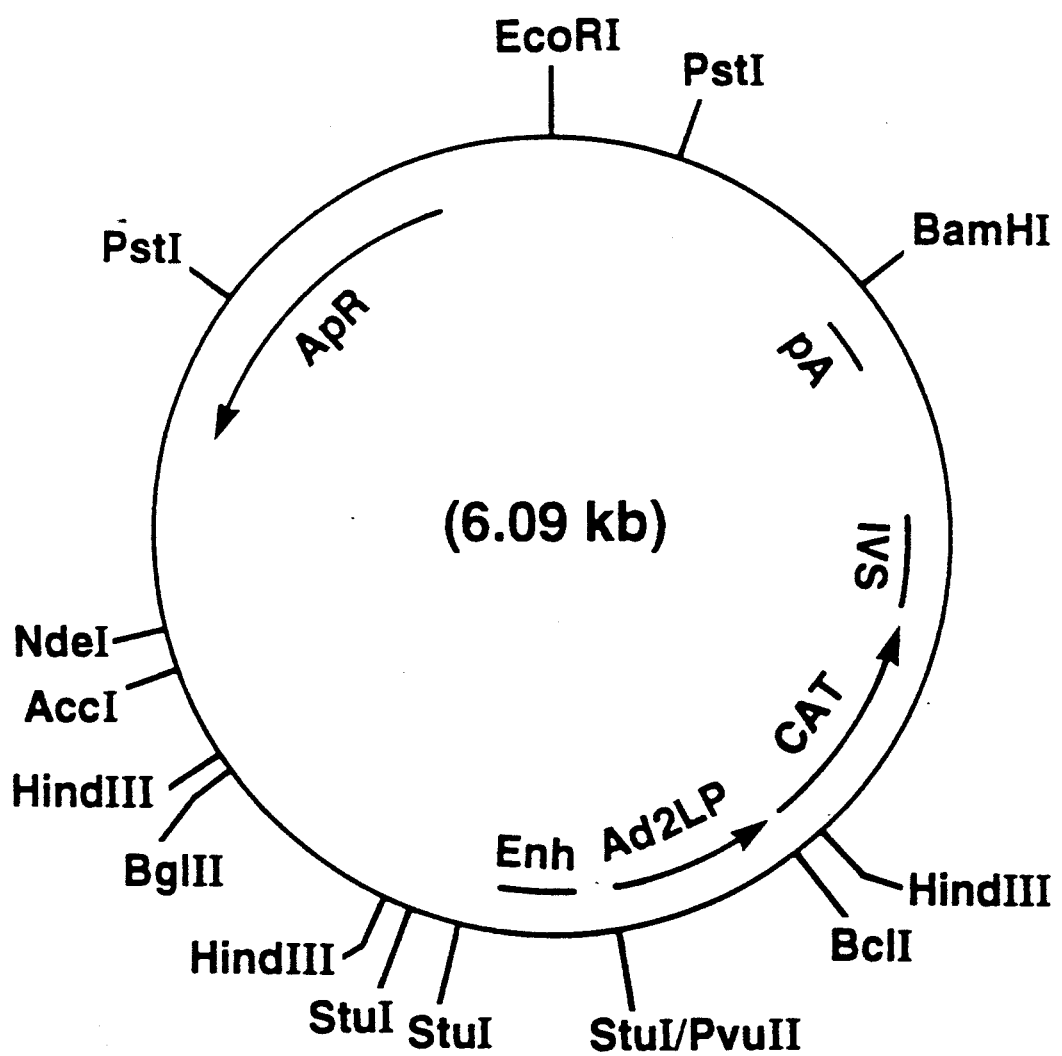
FIG. 13 is a restriction and function map of pBLcat.

The 5 μl of ~4.81 kb AccI-StuI restriction fragment of plasmid pLPcat were added to 5 μl of ~1.28 kb AccI-PvuII restriction fragment of plasmid pBKneo1. After the addition of 3 μl of 10X ligase buffer, 15 μl of $H_2O$, and 2 μl (about 1000 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 13 of the accompanying drawings.

The ligated DNA was used to transform *E. coli* K12 HB101 cells in substantial accordance with the procedure described in Example 1D. *E. coli* K12 HB101/pBLcat transformants were identified by restriction enzyme analysis of their plasmid DNA. Plasmid pBLcat DNA was prepared for use in subsequent constructions in substantial accordance with the procedure of Example 1F.

C. Final Construction of Plasmid pSBLcat

About 100 μg of plasmid pBLcat DNA were dissolved in 10 μl of 10X HindIII buffer (0.5M NaCl, 0.1M Tris-HCl (pH 8.0), 0.1M $MgCl_2$ and 1 mg/ml BSA) and 80 μl of $H_2O$. About 10 μl (about 100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was well separated from the other digestion products; then, the ~0.87 kb fragment was isolated from the gel, purified and ethanol precipitated. About 10 μg of the desired fragment were obtained and dissolved in 50 μl of TE buffer.

About 1 μg of plasmid pSV2cat DNA in 1 μl of TE buffer was dissolved in 2 μl of 10X HindIII buffer and 16 μl of $H_2O$. About 1 μl (about 10 units) of restriction enzyme HindIII was added to the solution of DNA, and the resulting reaction was incubated at 37° C. for 2 hours. The reaction was stopped by extracting the reaction mixture first with phenol, then twice with chloroform. The HindIII-digested plasmid pSV2cat DNA was precipitated with ethanol and resuspended in 100 μl of TE buffer. About 0.06 units of calf-intestinal alkaline phosphatase were added to the solution, and the resulting mixture was incubated at 37° C. for 30 minutes. The solution was adjusted to contain 1X SET (5 mM Tris-HCl (pH 7.8), 5 mM EDTA, and 150 mM NaCl), 0.3M sodium actate and 0.05% SDS and then incubated at 65° C. for 45 minutes. The DNA was extracted twice with phenol and then chloroform. The DNA was ethanol precipitated as described in Example 1 and the resuspended in 10 μl of TE buffer. The phosphatase treatment prevents the pSV2cat DNA from self-ligating.

Figure 14:
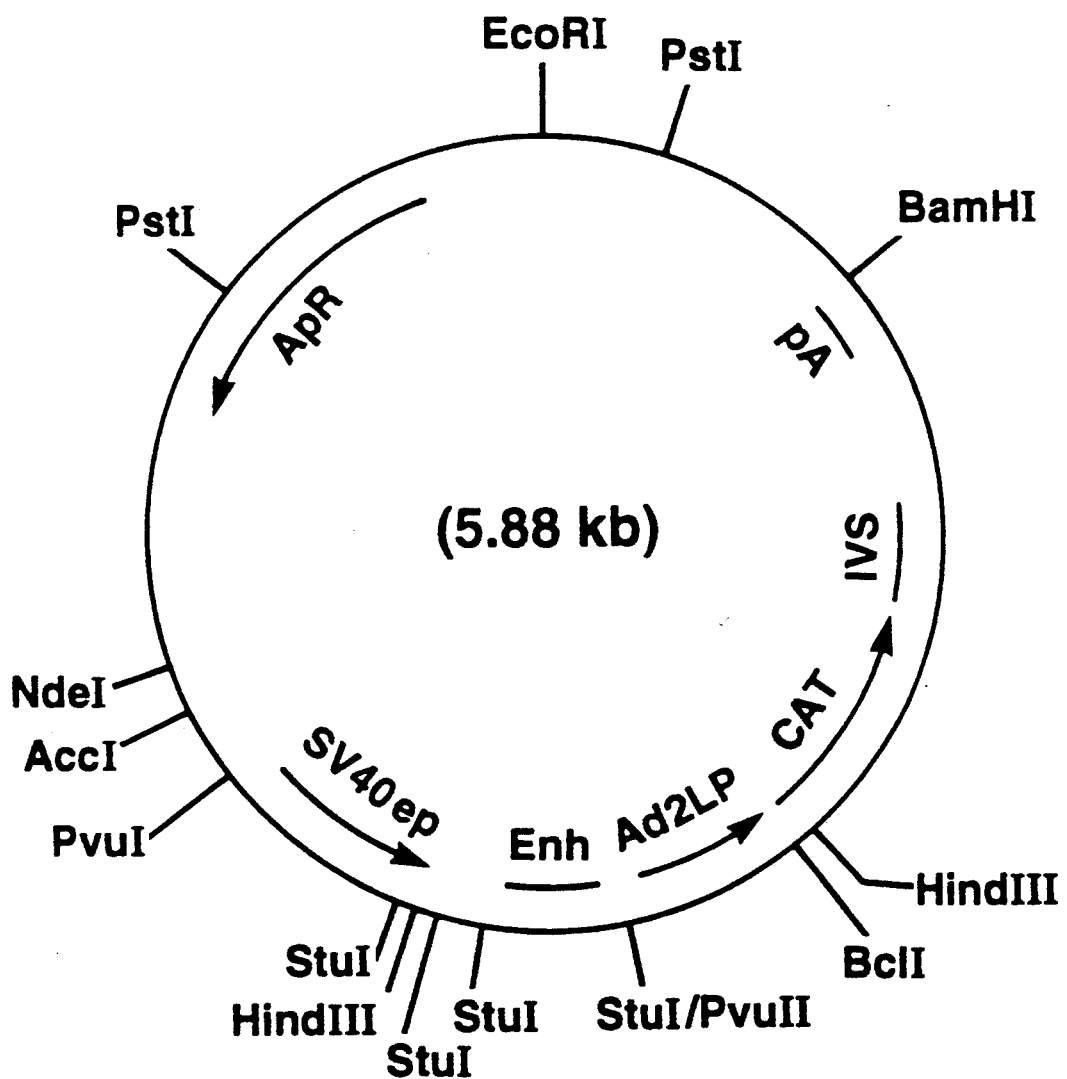
FIG. 14 is a restriction and function map of pSBLcat.

About 5 μl of the ~0.87 kb HindIII restriction fragment of plasmid pBLcat were added to the 10 μl of HindIII-digested plasmid pSV2cat, and then, 3 μl of 10X ligase buffer, 2 μl (about 1000 units) of T4 DNA ligase, and 13 μl of H₂O were added to the solution of DNA, and the resulting reaction was incubated at 16° C. for 2 hours. The ligated DNA constituted the desired plasmid pSBLcat. The ligated DNA was used to transform *Escherichia coli* K12 HB101 in substantial accordance with the procedure of Example 1D. The transformed cells were plated on L agar containing ampicillin, and the plasmid DNA of the ampicillin-resistant transformants was examined by restriction enzyme analysis to identify the *E. coli* K12 HB101/pSBLcat transformants. The ~0.87 kb HindIII restriction fragment that encodes the BK enhancer and Ad2 late promoter could insert into HindIII-digested plasmid pSBLcat in one of two orientations, only one of which yields plasmid pSBLcat. A restriction site and function map of plasmid pSBLcat is presented in FIG. 14 of the accompanying drawings.

Example 6

Construction of pSBL-Bt6-d

A. Preparation of the 3865 Base Pair AatII-XmaI Restriction Fragment of pmt6-hd

Twenty μg of pmt6-hd (prepared in Example 2) was digested to completion with 10 μl (20 units) of AatII in a 150 μl reaction volume containing 10 mM Tris-HCl (pH 7.5), 50 mM KCl, 10 mM MgCl₂ and 1 mM DTT. The sample was incubated at 37° C. for 3 hours. Following incubation, the sample was purified and collected by ethanol precipitation as described in Example 1A and resuspended in 210 μl of water.

The above DNA was digested to completion with XmaI as follows. Twenty-five μl of 10X BRL Core buffer (500 mM Tris-HCl (pH 8.0), 100 mM MgCl₂ and 500 mM NaCl) and 15 μl of XmaI (15 units) were added to the sample. The sample was mixed and then incubated at 37° C. for 16 hours. Following incubation, the sample was purified and collected as described in Example 1A and resuspended in 210 μl of water.

The above DNA was further digested with MstII to allow separation of the desired 3865 base pair AatII-BglII restriction fragment upon gel electrophoresis. Twenty-five μl of 10X MstII buffer (100 mM Tris-HCl (pH 7.5), 1.5M NaCl, 10 mM MgCl₂ and 2mM B-mercaptoethanol) and 15 μl of MstII (x units) were added to the sample. The sample was mixed and then incubated at 37° C. for 2 hours. Following incubation the 3865 base pair AatII-BglII restriction fragment was isolated by preparative gel electrophoresis.

B. Preparation of the 3228 Base Pair AatII-BclI Restriction Fragment of pSBLcat

The 3228 base pair AatII-BclI restriction fragment was isolated from the plasmid pSBL. The plasmid pSBL is a derivative of plasmid pSBLcat which was described in Example 5. The chloramphenical acetyl transferase (CAT) gene was deleted from pSBL cat to form pSBL. Alternatively, the 3228 base pair AatII-BclI restriction fragment can be isolated from pSBLcat as described below.

Twenty-five μg of pSBLcat (prepared in Example 4) is digested to completion with 20 μl (400 units) of AatII in a 200 μl reaction volume containing 10 mM Tris-HCl (pH 7.5), 50 mM KCl, 10 mM MgCl₂ and 1 mM DTT. The sample is incubated at 37° C. for 3 hours. Following incubation, 30 μl of 10X Core buffer (500 mM Tris-HCl (pH 8.0), 100 mM MgCl₂ and 500 mM NaCl), 60 μl of water and 10 μl (100 units) of BclI are added to the sample. The sample is incubated at 37° C. for 3 hours. Following incubation the 3228 base pair AatII-BclI restriction fragment is isolated by preparative gel electrophoresis.

C. Preparation of the 1190 Base Pair BamHI-XmaI Restriction Fragment of pTLB-t6

Twenty-five μg of pTLB-t6 (prepared in Example 3) was digested to completion in a reaction containing 20 μl (20 units) of XmaI, 5 μl of BamHI (50 units), 20 μl of 10X Core buffer (500 mM Tris-HCl (pH 8.0), 100 mM MgCl₂ and 500 mM NaCl) and 80 μl of water. The samples were incubated at 37° C. for 2 hours. Following incubation, the 1190 base pair BamHI-XmaI restriction fragment was isolated from each sample by preparative gel electrophoresis.

D. Final Preparation of Plasmids pSBL-Bt6-d

Fifty nanograms of the 3865 base pair AatII-XmaI restriction fragment of plasmid pmt6-hd (prepared in Example 6A) is ligated to 0.1 μg of the 3228 base pair AatI-BclI restriction fragment (prepared in Example 6B) and 0.05 μg of the 1190 base pair BamHI-XmaI restriction fragment of pTLB-t6 (prepared in Example 6C) in substantial accordance with the ligation method of Example 1C. A portion of the ligation mixture is used to transform *Escherichia coli* K12 AG1 in accordance with the method described in Example 1D. The transformants are selected on LB agar plates containing 100 μg/ml of ampicillin grown overnight at 37° C. Plasmid DNA is isolated from the ampicillin resistant clones by the DNA isolation procedure of Example 1E.

Figure 15:
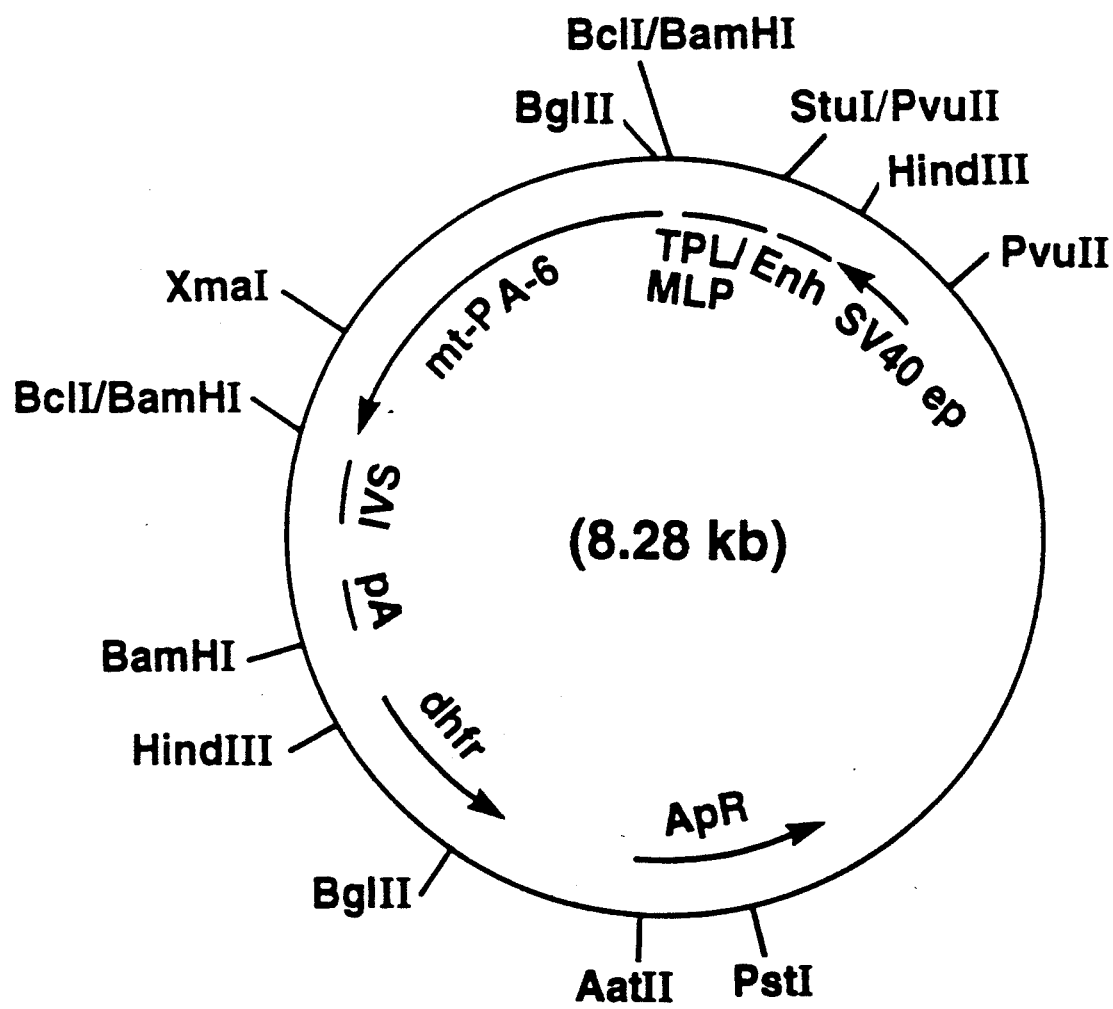
FIG. 15 is a restriction and function map of pSBL-Bt6.

A restriction site and function map of pSBL-Bt6-d is shown in FIG. 15.

Example 7

Construction of Plasmids pGT-t6B-d

A. Preparation of the 3865 Base Pair AatII-XmaI Restriction Fragment of pmt6-hd

The 3865 base pair AatII-XmaI restriction fragment of pmt6-hd was isolated as described in Example 6A.

B. Preparation of the 3560 Base Pair BclI-AatII Restriction Fragment of pGTC

The plasmid pGTC can be conventionally isolated from *Escherichia coli* K12 AG1/pGTC, a culture deposited on Jan. 18, 1990 and made part of the permanent stock culture collection of the Northern Regional Research Center (NRRL), Agricultural Research Service, U.S. Department of Agriculture, Peoria, Ill. 61604, under accession number NRRL B-18593. A restriction site and function map of pGTC is shown in FIG. 15.

The plasmid pGTC was transformed into the dam- cell line *Escherchia coli* K12 GM48 as described in Example 1D. *Escherichia coli* K12 GM48 is available from the NRRL under accession number NRRL B-15725. Other dam- cell lines may also be used. Plasmid DNA was isolated from these transformants as described in Example 1E.

Twenty-five μg of pGTC was digested to completion with 20 μl (40 units) of AatII in a 200 μl reaction volume containing 10 mM Tris-HCl (pH 7.5), 50 mM KCl, 10 mM MgCl$_2$ and 1 mM DTT. The sample was incubated at 37° C. for 3 hours. Following incubation, 30 μl of 10X Core buffer, 60 μl of water and 10 μl (100 units) of BclI were added to the sample. The sample was incubated at 37° C. for 3 hours. Following incubation the 3560 base pair AatII-BclI restriction fragment was isolated by preparative gel electrophoresis.

C. Preparation of the 1120 Base Pair BamHI-XmaI Restriction Fragment of pTLB-t6

The 1120 base pair BamHI-XmaI restriction fragment of pTLB-t6 was isolated as described in Example 6C.

D. Final Construction of pGT-t6B-d

Figure 16:
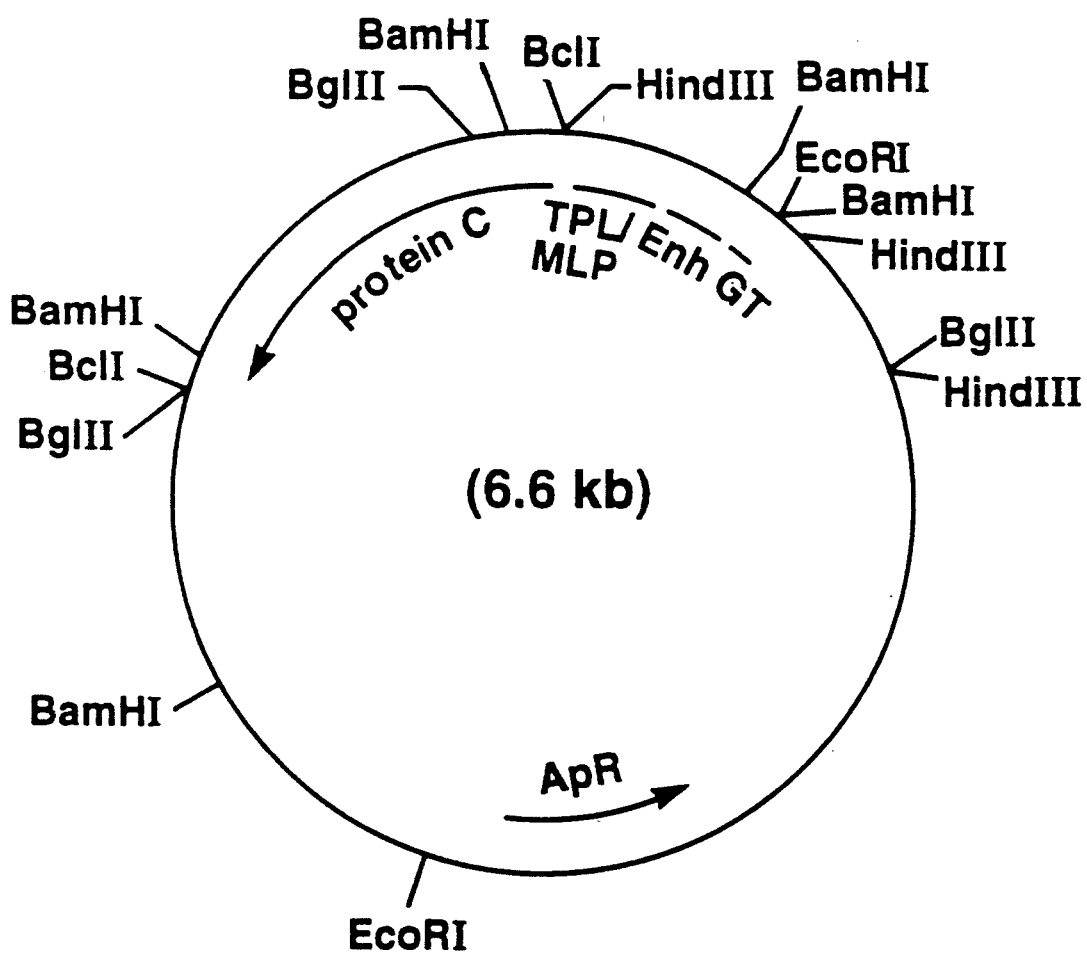
FIG. 16 is a restriction and function map of pGTC.
Figure 17:
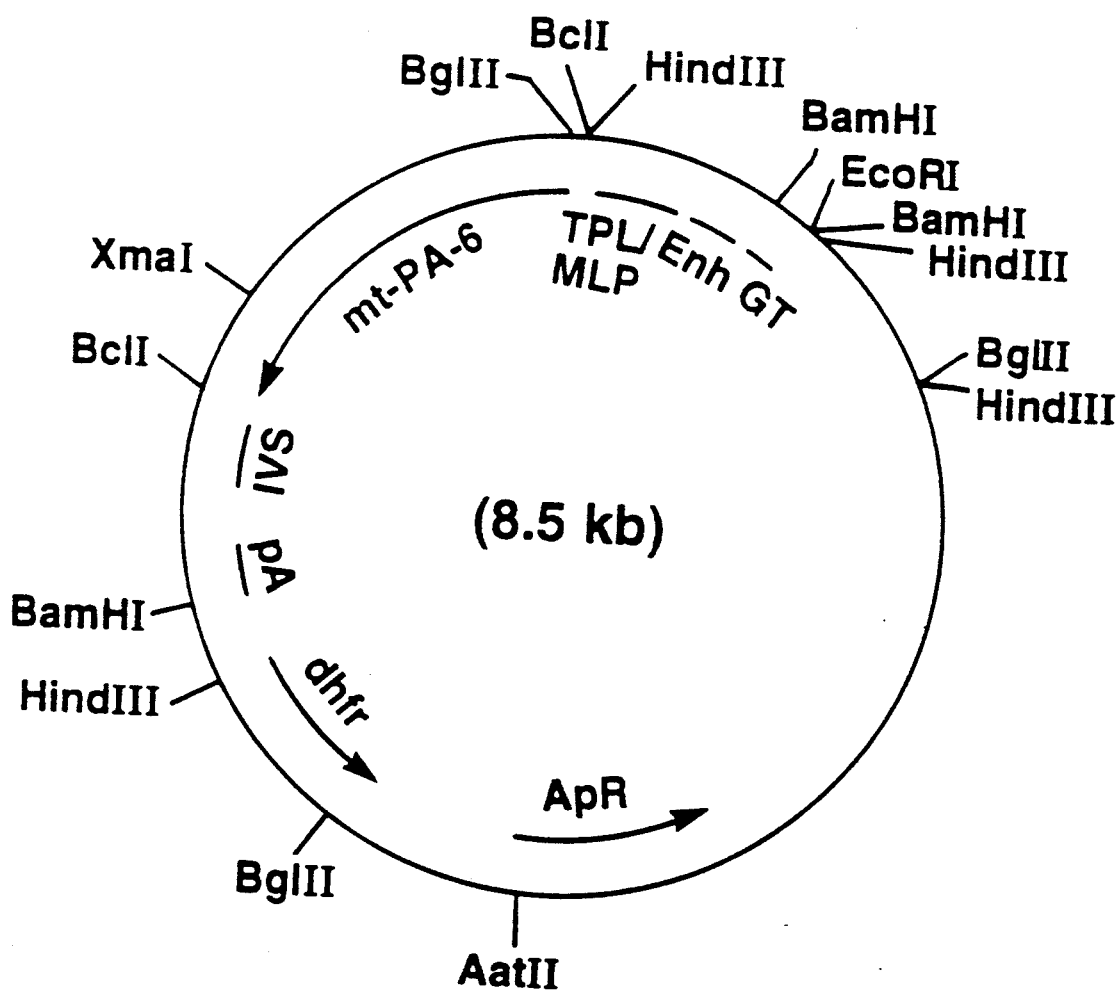
FIG. 17 is a restriction and function map of pGT-t6Bd.

Fifty ng of the AatII-XmaI restriction fragment of pmt6-hd (prepared in Example 7A) was ligated to 50 ng of the BclI-AatII restriction fragment of pGTC (prepared in Example 7B) and 50 ng of the BamHI-XmaI restriction fragment of pTLB-t6 (prepared in Example 7C) in substantial accordance with the ligation method of Example 1C. A portion of the ligation mixture was used to transform *Escherichia coli* K12 AG1 in accordance with the method described in Example 1D. The transformants were selected on LB agar plates containing 100 μg/ml of ampicillin grown overnight at 37° C. Plasmid DNA was isolated from the ampicillin resistant clones by the DNA isolation procedure of Example 1E. A restriction site and function map of pGT-t6B-d is shown in FIG. 16.

Example 8

Transformation and Culturing

A. Transformation of AV12-664 Cells

The transformation procedure described below refers to AV12-664 cells as the host cell line; however, the procedure is generally applicable to most eukaryotic cell lines.

AV12-664 cells are obtained from the ATCC under the accession number CRL 9595 in a 25 mm$^2$ flask Containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco, 3175 Staley Road, Grand Island, N.Y. 14072), adding 0.25% trypsin for 1-2 minutes, rinsing with fresh medium, aspirating, and dispensing into new flasks at a subcultivation ratio of 1:5 or 1:10.

One day prior to transformation, cells are seeded at $0.7 \times 10^6$ cells per 100 mm or 55 cm$^2$ dish. The medium is changed 4 hours prior to transformation. Sterile, ethanol-precipitated plasmid DNA dissolved in H$_2$O is used to prepare a 2X DNA-CaCl$_2$ solution containing 20 μg/ml DNA and 250 mM CaCl$_2$. 2X HBS is prepared containing 280 mM NaCl, 50 mM Hepes (N-2-Hydroxyethylpiperazine-N'-2-ethanesulfonic acid), and 1.5 mM sodium phosphate, with the pH adjusted to 7.05-7.15. The 2X DNA-CaCl$_2$ solution is added dropwise to an equal volume of sterile 2X HBS with a one ml sterile plastic pipette with a cotton plug while air is slowly bubbled through the solution. The calcium-phosphate-DNA precipitate is allowed to form without further agitation for 30-45 minutes at room temperature.

The precipitate is then mixed by gentle pipetting with a plastic pipette, and 0.5 ml (per plate) of precipitate is added directly to the 10 ml of growth medium that covers the recipient cells. After 4 hours of incubation at 37° C., the medium is replaced with DMEM containing 10% fetal bovine serum and the cells are allowed to incubate for an additional 72 hours before providing selective pressure. For plasmids that do not comprise a selectable marker that functions in eukaryotic cells, the transformation procedure utilizes a mixture of plasmids: the expression vector of the invention but lacking a selectable marker; and an expression vector that comprises a selectable marker that functions in eukaryotic cells. This co-transformation technique allows for the identification of cells that comprise both of the transforming plasmids by isolating colonies that grow in the presence of the selective pressure and assaying for the useful protein.

For cells transfected with plasmids containing the hygromycin resistance-conferring gene, hygromycin is added to the growth medium to a final concentration of about 200 to 400 μg/ml. AV12-664 cells can also be directly selected with methotrexate (200-500 nM) when transformed with a vector containing the murine dhfr gene. The cells are then incubated at 37° C. for 2-4 weeks with medium changes at 3 to 4 day intervals. The resulting hygromycin-resistant or methotrexate resistant colonies are transferred to individual culture flasks for characterization.

Example 9

Demonstration of Efficacy

The tissue plasminogen activator molecules of the present invention are isolated from the culture medium by methods well known in the art such as described by Burck et al., supra. The two forms of mt-PA6 can be separated by affinity chromatography in substantial accordance with the method of Einarsson et al., 1985, *Biochim. Biophys. Acta* 830:1-10, and Rijken et al., 1985, *Thromb. and Haemostas.* 54(4), 788-791. Preferably, Variant mt-PA6 is isolated by preparative hydrophobic interaction chromatography using a TSK phenyl-5PW column (20 mm ID×150 mm long) as follows. Mobile Phase A was 1M potassium phosphate, 2M urea, 0.02% sodium azide, pH 8.5. Mobile Phase B was the same as Mobile Phase A except that the potassium phosphate concentration was 0.02M. The plasminogen activator was applied to the column in 50% Mobile Phase A/50% Mobile Phase B. The separation was performed using an initial eluent composition of 20% Mobile Phase B. After 15 minutes the eluent composition was increased to 50% Mobile Phase B, and then to Mobile Phase B. The fractions were acidified to pH 3 with HCl, dialyzed against 0.001M HCl/0.001% Tween 80, and lyopholized. The fractions were stored at 20° C.

Efficacy of the method of the present invention was studied in a canine thrombosis model in substantial accordance with the methods described by Jackson, et al., supra. Methods used in the measurement of systemic plasminogen and fibrinogen degradation and the in vivo studies of reperfusion and flow maintenance were also described by Jackson, et al., supra.

Plasma samples from the canine thrombosis model were analyzed for the single-chain and two-chain forms of Variant mt-PA6. The chain composition of immuno-captured Variant mt-PA6 can be analyzed based upon the fact that two-chain plasminogen activator forms hydrolyze S-2288 (H-D-Ile-Pro-Arg-pNA) markedly faster than single-chain plasminogen activator forms. Accordingly, S-2288 was added to a plate (Plate #1) containing immuno-captured Variant mt-PA6 and the immuno-captured Variant mt-PA6 hydrolysis of S-2288 was measured. Additionally, all immuno-captured Variant mt-PA6 in a second plate (Plate #2) was converted to the two-chain form by treatment with trace amount of plasmin reagent. S-2288 was then added to this plate and the immuno-captured, two-chain Variant mt-PA6 hydrolysis of S-2288 was measured. The difference in S-2288 hydrolytic activity observed between Plate #1 and Plate #2 is proportional to the amount of single-chain Variant mt-PA6 present in the sample. Quantitative analysis is accomplished by placing reference standard single-chain native t-PA (in a series of known concentrations) in wells of both Plate #1 and Plate #2 and using the observed changes in the reference standards to assign quantitative numbers with respect to the unknown samples.

A Biomek 1000 Laboratory Workstation Automated Sample Handler (Beckman) is used to perform all steps of the assay including the addition of diluted samples and standards to the assay plates, the addition of all assay reagents, and the performance of plate washing procedures. Variant mt-PA6 was immuno-captured from plasma samples of the canine thrombosis model in substantial accordance with the method of Jackson et al., supra. The S-2288 substrate (Helena Laboratories, #5279) was prepared by mixing 1 ml of a 3 mM stock (in water) with 15 ml buffer (0.5M Tris, 0.001% Tween 80, pH 8.8). Trasylol (Mobay Chemical Corporation) was added to a final concentration of 20 KIU/ml.

Two hundred µl of the S-2288 substrate was added to the wells of a plate (Plate #1) in which Variant mt-PA6 from the plasma samples of the canine thrombosis model had been immuno-captured. The optical density at 405 nm at room temperature was measured with a Vmax plate reader (Molecular Devices, Inc., Palo Alto, Calif.). Ten µl samples of 1-6 ng/ml require 20 hours reaction time. Ten µl samples of 100–1000 ng/ml require 6-9 hours of reaction time. The data from these measurements were analyzed by curve fitting programs Softmax (Molecular Devices, Inc.).

Two-hundred µl of a 10 nM plasmin solution (10 µl of a 2 mg/ml plasmin stock (America Diagnostica, #411) in 20.1 ml of 0.03M Tris/0.15M NaCl, pH 7.4) was added to the wells of a second plate (Plate #2) containing immuno-captured Variant mt-PA6 of plasma samples from the canine thrombosis model. Plate #2 was incubated at room temperature for 1 hour while gently mixing. The plate was then washed four times with PET buffer (American Diagnostica, kit No. 122). Two-hundred µl of the S-2288 substrate was added to the wells. The optical density was measured and the data analyzed as above.

As depicted in Table 1, there is a remarkable distinction in the pharmacological properties of Variant and Primary mt-PA6. Dogs treated with Primary mt-PA6 demonstrated 80% to 90% decrease in plasma fibrinogen. Surprisingly, the dogs treated with Variant mt-PA6 demonstrated a much less substantial decrease in fibrinogen.

Table 1 also shows that the Primary mt-PA6 treated dogs demonstrated a greater decrease in plasma plasminogen levels as compared to Variant mt-PA6. This is consistent with the fact that plasminogen decrease (which indicates plasminogen activation and subsequent inactivation by $\alpha_2$-antiplasmin) precedes fibrinogen degradation. None of the dogs treated with Variant mt-PA6 showed significant plasminogen decreases.

Further in vivo testing indicated that dogs reperfused with Variant mt-PA6 demonstrated significantly greater maintenance of coronary blood flow than dogs treated with Primary mt-PA6 (Table 2). Also, in dogs treated with Variant mt-PA6, the single chain form exists for a longer period of time than does the single chain form of Primary mt-PA6 (Table 3).

TABLE 1

Measure of Systemic Plasminogen and Fibrinogen Degradation (0.45 mg/kg, Bolus)

|  | Dog # | Fibrinogen (mg/ml) start | Fibrinogen (mg/ml) end | Plasminogen (% of base) |
|---|---|---|---|---|
| Variant | 6248 | 3.2 | 2.7 | 99 |
|  | 6348 | 2.9 | 2.9 | 98 |
|  | 6345 | 4.2 | 2.4 | 98 |
|  | 6349 | 3.3 | 3.1 | 96 |
| Primary | 6245 | 2.9 | 0.4 | 76 |
|  | 6347 | 2.7 | 0.3 | 74 |
|  | 6399 | 2.7 | 0.3 | 59 |

Variant = 85% Variant, 12% Primary
Primary = 92% Primary, 5.5% Variant

TABLE 2

In vivo Comparison of Variant and Primary Forms of mt-PA6 (0.45 mg/kg)

|  | Dog # | Time to Reperfusion (min.) | Flow Maintenance (% Pre-stimulation Flow) |
|---|---|---|---|
| Variant | 6345 | 27 | 56 |
|  | 6248 | 13 | 73 |
|  | 6348 | 16 | 59 |
| Primary | 6245 | 42 | 34 |
|  | 6399 | 8 | 25 |
|  | 6437 | 38 | 21 |

Variant = 85% Variant, 12% Primary
Primary = 91% Primary, 5.5% Variant

TABLE 3

Measure of Single Chain Metabolism (0.45 mg/kg, Bolus)

|  | Dog # | Single Chain (%) t = 0 | t = 30 | t = 60 | End |
|---|---|---|---|---|---|
| Variant | 6248 | 100 | 75 | 65 | 60 |
|  | 6348 | 100 | 80 | 60 | 40 |
|  | 6345 | 100 | 80 | 55 | 45 |
| Primary | 6245 | 100 | 70 | 15 | 0 |

Variant = 85% Variant, 12% Primary
Primary = 92% Primary, 5.5% Variant

---

We claim:

1. A method of treating thromboembolic disorders which comprises administering a thrombolytically effective dose of t-PA derivative molecules that lack the Finger, EGF and Kringle 1 domains wherein the majority of the molecules comprising said dose are diglycosylated.

2. The method of treating thromboembolic disorders of claim 1 by administration of a thrombolytically effective dose of Variant mt-PA6.

3. A method of claim 1 wherein the dose of said t-PA derivative molecules is about 0.01 mg/kg to 10 mg/kg.

4. A method of claim 1 wherein the dose of said t-PA derivative molecules is about 0.1 mg/kg to 1 mg/kg.

5. A method of claim 2 wherein the dose of Variant mt-PA6 is about 0.01 mg/kg to 10 mg/kg.

6. A method of claim 2 wherein the dose of Variant mt-PA6 is about 0.1 mg/kg to 1 mg/kg.

7. A method of claim 2 wherein the dose of Variant mt-PA6 is about 0.4 mg/kg.

8. The method of claim 1 wherein the thromboembolic disorder is selected from the group comprising deep vein thrombosis, disseminated intravascular coagulation, emboli originating from the heart or peripheral arteries, acute myocardial infarction, thrombotic strokes, and fibrin deposits associated with invasive cancers.

9. The method of claim 2 wherein the thromboembolic disorder is selected from the group comprising deep vein thrombosis, disseminated intravascular coagulation, emboli originating from the heart or peripheral arteries, acute myocardial infarction, thrombotic strokes, and fibrin deposits associated with invasive cancers.

10. A composition comprising a thrombolytically effective dose of t-PA derivative molecules that lack the Finger, EGF and Kringle 1 domains in admixture with a pharmaceutically acceptable carrier, wherein greater than 85% of said molecules are diglycosylated.

11. The composition of claim 10 that comprises an effective dose of Variant mt-PA6 in admixture with a pharmaceutically acceptable carrier.

* * * * *

UNITED STATES PATENT AND TRADEMARK OFFICE
CERTIFICATE OF CORRECTION

PATENT NO. : 5,242,688
DATED : September 7, 1993
INVENTOR(S) : Philip J. Burck, et al It is certified that error appears in the above-indentified patent and that said Letters Patent is hereby corrected as shown below:

Column 39, lines 33-34, "the majority" should read -- greater than 85% --.

Signed and Sealed this

Twenty-fourth Day of October, 1995

Attest:

BRUCE LEHMAN

Attesting Officer          Commissioner of Patents and Trademarks

SEQUENCE LISTING ( 1 ) GENERAL INFORMATION:

(i i i) NUMBER OF SEQUENCES:12

(2) INFORMATION FOR SEQ ID NO:1:

(i) SEQUENCE CHARACTERISTICS:
        (A) LENGTH:5 amino acids
        (B) TYPE:amino acid
        (C) TOPOLOGY:linear (i i) MOLECULE TYPE:peptide (i x) FEATURE: Xaa is Lys or Arg (x i) SEQUENCE DESCRIPTION: SEQ ID NO:1:

Arg Ile Xaa Xaa Xaa
1               5

(2) INFORMATION FOR SEQ ID NO:2:

(i) SEQUENCE CHARACTERISTICS:
        (A) LENGTH:5 amino acids
        (B) TYPE:amino acid
        (C) TOPOLOGY:linear (i i) MOLECULE TYPE:peptide (i x) FEATURE: Xaa is Lys or Arg (x i) SEQUENCE DESCRIPTION: SEQ ID NO:2:

Ser Arg Xaa Xaa Xaa
1               5

(2) INFORMATION FOR SEQ ID NO:3:

(i) SEQUENCE CHARACTERISTICS:
        (A) LENGTH:5 amino acids
        (B) TYPE:amino acid
        (C) TOPOLOGY:linear (i i) MOLECULE TYPE:peptide (i x) FEATURE: Xaa is Lys or Arg (x i) SEQUENCE DESCRIPTION: SEQ ID NO:3:

Glu Arg Xaa Xaa Xaa
1               5

(2) INFORMATION FOR SEQ ID NO:4:

(i) SEQUENCE CHARACTERISTICS:
        (A) LENGTH:5 amino acids
        (B) TYPE:amino acid
        (D) TOPOLOGY:linear (i i) MOLECULE TYPE:peptide (i x) FEATURE:Xaa is Lys or Arg (x i) SEQUENCE DESCRIPTION: SEQ ID NO:4:

Val Arg Xaa Xaa Xaa
1               5

(2) INFORMATION FOR SEQ ID NO:5:

(i) SEQUENCE CHARACTERISTICS:
        (A) LENGTH:5 amino acids
        (B) TYPE:AMINO ACID
        (D) TOPOLOGY:linear (i i) MOLECULE TYPE:peptide (x i) SEQUENCE DESCRIPTION: SEQ ID NO:5:

Arg Ile Arg Lys Arg
1              5

( 2 ) INFORMATION FOR SEQ ID NO:6:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:6:

Ser Arg Lys Arg Arg
1              5

( 2 ) INFORMATION FOR SEQ ID NO:7:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:7:

Glu Arg Arg Lys Arg
1              5

( 2 ) INFORMATION FOR SEQ ID NO:8:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( x i ) SEQUENCE DESCRIPTION: SEQ ID NO:8:

Val Arg Lys Arg Arg
1              5

( 2 ) INFORMATION FOR SEQ ID NO:9 :

( i ) SEQUENCE CHARACTERISTICS:
        ( A ) LENGTH:114 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:9:

```
GATCCGCCAC  CATGGATGCA  ATGAAGAGAG  GGCTCTGCTG  TGTGCTGCTG   50
CTGTGTGGAG  CAGTCTTCGT  TTCGCCCAGC  CAGGAAATCC  ATGCCCGATT  100
CAGAATCCGA  AAAA                                            114
```

( 2 ) INFORMATION FOR SEQ ID NO:10 :

( i ) SEQUENCE CHARACTERISTICS:
        ( A ) LENGTH:114 nucleotides
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO:10:

```
GATCTTTTGC  GGATTCTGAA  TCGGGCATGG  ATTTCCTGGC  TGGGCGAAAC   50
GAAGACTGCT  CCACACAGCA  GCAGCACACA  GCAGAGCCCT  CTCTTCATTG  100
CATCCATGG   TGGCG                                           114
```

(2) INFORMATION FOR SEQ ID NO:11:

(i) SEQUENCE CHARACTERISTICS:
(A) LENGTH: 287 nucleotides
(B) TYPE:nucleic acid
(C) STRANDEDNESS:double
(D) TOPOLOGY:linear
(ii) MOLECULE TYPE:DNA
(xi) SEQUENCE DESCRIPTION: SEQ ID NO:11:

| | | | | |
|---|---|---|---|---|
| AATTCACGCT | GTGGTGTTAT | GGTCGGTGGT | CGCTAGGGTG | 40 |
| CCGACGCGCA | TCTCGACTGC | ACGGTGCACC | AATGCTTCTG | 80 |
| GCGTCAGGCA | GCCAATCGGA | AGCTGTGGTA | TGGCTGTGCA | 120 |
| GGTCGTATAA | TCACCGCATA | ATTCGAGTCG | CTCAAGGCGC | 160 |
| ACTCCCGTTC | CGGATAATGT | TTTTTGCTCC | GACATCATAA | 200 |
| CGGTTCCGGC | AAATATTCTG | AAATGAGCTG | TTGACAATTA | 240 |
| ATCATCGAAC | TAGTTAACTA | GTACGCAAGT | TCTCGTAAAA | 280 |
| AGGGTAT | | | | 287 |

(2) INFORMATION FOR SEQ ID NO:12:

(i) SEQUENCE CHARACTERISTICS:
(A) LENGTH:36 nucleotides
(B) TYPE:nucleic acid
(C) STRANDEDNESS:single
(D) TOPOLOGY:linear
(ii) MOLECULE TYPE:DNA
(xi) SEQUENCE DESCRIPTION: SE. ID NO:12:

GGAGCCAGAT CTTACCAAGG AAACAGTGAC TGCTAC    36